United States Patent
Matsuda et al.

(10) Patent No.: US 11,865,214 B2
(45) Date of Patent: Jan. 9, 2024

(54) IBUDILAST ORAL FORMULATIONS AND METHODS OF USING SAME

(71) Applicant: MediciNova, Inc., La Jolla, CA (US)

(72) Inventors: Kazuko Matsuda, La Jolla, CA (US); Federico Carlos Aréjola Gaeta, Málaga (ES)

(73) Assignee: MediciNova, Inc., La Jolla, CA (US)

( * ) Notice: Subject to any disclaimer, the term of this patent is extended or adjusted under 35 U.S.C. 154(b) by 467 days.

(21) Appl. No.: 17/027,567

(22) Filed: Sep. 21, 2020

(65) Prior Publication Data

US 2021/0085613 A1 Mar. 25, 2021

Related U.S. Application Data

(60) Provisional application No. 62/904,519, filed on Sep. 23, 2019.

(51) Int. Cl.
*A61K 9/28* (2006.01)
*A61K 9/48* (2006.01)
*A61K 31/437* (2006.01)
*A61K 9/00* (2006.01)

(52) U.S. Cl.
CPC .......... *A61K 9/2826* (2013.01); *A61K 9/2866* (2013.01); *A61K 9/4816* (2013.01); *A61K 31/437* (2013.01); *A61K 9/0053* (2013.01)

(58) Field of Classification Search
None
See application file for complete search history.

(56) References Cited

U.S. PATENT DOCUMENTS

| | | | |
|---|---|---|---|
| 6,395,747 B1 | 5/2002 | Sakoda et al. | |
| 8,138,201 B2 | 3/2012 | Kalafer et al. | |
| 9,314,452 B2 | 4/2016 | Kalafer et al. | |
| 2006/0160843 A1 | 7/2006 | Johnson et al. | |
| 2010/0102474 A1* | 4/2010 | Nakashima | A61K 9/2077 264/134 |

FOREIGN PATENT DOCUMENTS

| | | |
|---|---|---|
| EP | 2 090 298 A1 | 8/2009 |
| JP | H0920663 A | 1/1997 |
| KR | 100780479 B1 | 11/2007 |
| KR | 2009 0082608 A * | 7/2009 ............... A61K 9/20 |
| WO | WO-2006111981 A2 * | 10/2006 ............. A61K 9/284 |
| WO | WO 2011/122899 A2 | 10/2011 |

OTHER PUBLICATIONS

English translation (Google) of KR 2009 0082608 (A)—Jul. 31, 2009 (8 pages) (Year: 2009).*
Foreign Search Report issued in International Patent Application No. PCT/US2020/051753, dated Jan. 13, 2021.
Cho, et al., "Allosteric Inhibition of Macrophage Migration Inhibitory Factor Revealed by Ibudilast," *PNAS*, vol. 107, No. 25, pp. 11313-11318 (2010).
Gibson et al., "The Inhibitory Profile of Ibudilast Against the Human Phosphodiesterase Enzyme Family," European Journal of Pharmacology, vol. 538, pp. 39-42 (2006).
Sanftner et al., "Cross-species comparisons of the pharmacokinetics of ibudilast," Xenobiotica, vol. 39, No. 12, pp. 964-977 (Nov. 2009). [Abstract].
Mizuno et al., "Neuroprotective role of phosphodiesterase inhibitor ibudilast on neuronal cell death induced by activated microglia," Neuropharmacology, vol. 46, pp. 404-411(2004).
Obernolte, R., et al. (1993) "The cDNA of a human lymphocyte cyclic-AMP phosphodiesterase (PDE IV) reveals a multigene family" Gene 129: 239-247.
Rile et al., "Potentiation of Ibudilast Inhibition of Platelet Aggregation in the Presence of Endothelial Cells," Thrombosis Research, 102 239-246 (2001).
Souness et al., "Possible Role of Cyclic AMP Phosphodiesterases in the Actions of Ibudilast on Eosinophil Thromboxane Generation and Airways Smooth Muscle Tone," British Journal of Pharmacology, 111:1081-1088 (1994).
Suzumura et al., "Ibudilast suppresses TNF alpha. production by glial cells functioning mainly as type III phosphodiesterase inhibitor in NCS," Brain Research, 837:203-212 (1999).
Takuma et al., "Ibudilast attenuates actrocyte apoptsis via cyclic GMP signaling pathway in an in vitro reperfusion model," British Journal of Pharmacology, 133:841-848 (2001).
Jeffery et al., "The preparation and characterization of poly(lactide-co-glycolide) microparticles. II. The Entrapment of a Model Protein Using a (water-in-oil)-in-water Emulsion Solvent Evaporation Technique," Pharm. Research, vol. 10, pp. 362-368 (1993).
Yang, et al., "The Emerging Role of Toll-Like Receptor 4 in Myocardial Inflammation," *Cell Death and Disease*, vol. 7, e2234, 10 pages (2016).
MediciNova Starts Phase II Clinical Trial of MN-166 for Multiple Sclerosis, News. Medical.Net; Pharmaceutical News, Aug. 2, 2005.

* cited by examiner

*Primary Examiner* — Aradhana Sasan
(74) *Attorney, Agent, or Firm* — Foley & Lardner LLP

(57) ABSTRACT

This disclosure is directed to ibudilast higher dosage oral formulations, such as tablet or capsule formulations, and the corresponding methods of treatment.

10 Claims, No Drawings

IBUDILAST ORAL FORMULATIONS AND METHODS OF USING SAME

CROSS-REFERENCE TO RELATED APPLICATIONS

This application claims the benefit of U.S. Provisional Patent Application No. 62/904,519, filed Sep. 23, 2019, which is incorporated by reference herein in its entirety.

BACKGROUND

The small molecule ibudilast (3-isobutyryl-2-isopropylpyrazolo[1,5-a]pyridine) is an inhibitor of macrophage inhibitory factor (MIF) (Cho et al., PNAS-USA, 2010 June 107: 11313-8), is a selective inhibitor of cyclic nucleotide phosphodiesterases (PDEs) 3A, 4, 10A1 and 11A1 (Gibson et al., Eur. J. Pharmacol., 538: 39-42, 2006), and has toll-like receptor-4 (TLR4) antagonistic activity (Yang et al., Cell Death and Disease (2016) 7, e2234; doi:10.1038/cddis.2016.140). Ibudilast distributes well to the CNS (Sanftner et al., Xenobiotica, 2009 39: 964-977) and at clinically-relevant plasma or CNS concentrations, ibudilast selectively inhibits macrophage migration inhibitory factor (MIF) and, secondarily, PDEs 3, 4, 10 and 11. Ibudilast also acts as a leukotriene D4 antagonist, an anti-inflammatory, a PAF antagonist, and a vasodilatory agent (Thompson Current Drug Reports). Ibudilast is thought to exert a neuroprotective role in the central nervous system of mammals, presumably via suppression of the activation of glial cells (Mizuno et al., Neuropharmacology 46: 404-411, 2004).

Ibudilast has been widely used in Japan for relieving symptoms associated with ischemic stroke or bronchial asthma. In recent clinical trials, its use in the treatment of multiple sclerosis (MS), an inflammatory disease of the central nervous system, has been explored (News.Medical.Net; Pharmaceutical News, 2 Aug. 2005). As disclosed in this publication, this clinical trial was expected to treat "relapsing-remitting MS," however, no mention is made of progressive multiple sclerosis. In U.S. Pat. No. 6,395,747, ibudilast is disclosed as a treatment for multiple sclerosis, which is generally understood to mean relapsing and remitting multiple sclerosis, not progressive multiple sclerosis. U.S. Patent Application Publication No. 20060160843 discloses ibudilast for the treatment of intermittent and short term pain, however, this is not pain related to a progressive neurodegenerative disease. However, U.S. Pat. No. 9,314,452 discloses ibudilast as a treatment for amyotrophic lateral sclerosis, a progressive neurodegenerative disease. Similarly, U.S. Pat. No. 8,138,201 discloses ibudilast as a treatment for primary progressive multiple sclerosis and/or secondary progressive multiple sclerosis.

SUMMARY

Provided herein in one aspect is a pharmaceutical composition comprising ibudilast and at least one pharmaceutically acceptable excipient, wherein said pharmaceutical composition is in the form of a tablet or a capsule, and wherein said tablet or said capsule has a dissolution profile wherein at least about 12% of said ibudilast has been released from said tablet or said capsule at about 2 hours when tested in USP Apparatus Type II at 50 rpm in 900 mL of simulated gastric fluid medium at 37° C. In some embodiments, the tablet has a coating comprising polyvinyl alcohol, plasticizer, and pigment. In some embodiments, the at least one pharmaceutically acceptable excipient comprises microcrystalline cellulose, lactose, or hypromellose, or any combination of two or more thereof. In some embodiments, said tablet or said capsule has a dissolution profile wherein at least about 25% of said ibudilast has been released from said tablet or said capsule at about 4 hours when tested in USP Apparatus Type II at (a) 50 rpm in 900 mL of simulated gastric fluid medium at 37° C. for 2 hours, followed by (b) 50 rpm in 900 mL of phosphate buffer with 0.3% w/w sodium lauryl sulfate at a pH of 6.8 at 37° C. for another 2 hours. In some embodiments, said tablet or said capsule has a dissolution profile wherein at least about 60% of said ibudilast has been released from said tablet or said capsule at about 12 hours when tested in USP Apparatus Type II at (a) 50 rpm in 900 mL of simulated gastric fluid medium at 37° C. for 2 hours, followed by (b) 50 rpm in 900 mL of phosphate buffer with 0.3% w/w sodium lauryl sulfate at a pH of 6.8 at 37° C. for another 10 hours. In some embodiments, said tablet or said capsule has a dissolution profile wherein at least about 90% of said ibudilast has been released from said tablet or said capsule at about 24 hours when tested in USP Apparatus Type II at (a) 50 rpm in 900 mL of simulated gastric fluid medium at 37° C. for 2 hours, followed by (b) 50 rpm in 900 mL of phosphate buffer with 0.3% w/w sodium lauryl sulfate at a pH of 6.8 at 37° C. for another 22 hours. In some embodiments, said tablet or said capsule comprises from about 10 mg to about 100 mg of said ibudilast.

Provided herein in another aspect is a pharmaceutical composition comprising ibudilast and at least one pharmaceutically acceptable excipient, wherein said pharmaceutical composition is in the form of a tablet or a capsule, and wherein said tablet or said capsule has a dissolution profile wherein no ibudilast has been released from said tablet or said capsule at about 2 hours when tested in USP Apparatus Type II at 50 rpm in 900 mL of simulated gastric fluid medium at 37° C. In some embodiments, the tablet has a coating comprising methacrylic acid and ethyl acrylate copolymer dispersion; triethyl citrate; and talc. In some embodiments, the at least one pharmaceutically acceptable excipient comprises microcrystalline cellulose, lactose, or hypromellose, or any combination of two or more thereof. In some embodiments, said tablet or said capsule has a dissolution profile wherein about 10% to about 20% of said ibudilast has been released from said tablet or said capsule at about 4 hours when tested in USP Apparatus Type II at (a) 50 rpm in 900 mL of simulated gastric fluid medium at 37° C. for 2 hours, followed by (b) 50 rpm in 900 mL of phosphate buffer with 0.3% w/w sodium lauryl sulfate at a pH of 6.8 at 37° C. for another 2 hours. In some embodiments, said tablet or said capsule has a dissolution profile wherein about 55% to about 65% of said ibudilast has been released from said tablet or said capsule at about 12 hours when tested in USP Apparatus Type II at (a) 50 rpm in 900 mL of simulated gastric fluid medium at 37° C. for 2 hours, followed by (b) 50 rpm in 900 mL of phosphate buffer with 0.3% w/w sodium lauryl sulfate at a pH of 6.8 at 37° C. for another 10 hours. In some embodiments, said tablet or said capsule has a dissolution profile wherein about 85% to about 95% of said ibudilast has been released from said tablet or said capsule at about 24 hours when tested in USP Apparatus Type II at (a) 50 rpm in 900 mL of simulated gastric fluid medium at 37° C. for 2 hours, followed by (b) 50 rpm in 900 mL of phosphate buffer with 0.3% w/w sodium lauryl sulfate at a pH of 6.8 at 37° C. for another 22 hours. In some embodiments, said tablet or said capsule comprises from about 10 mg to about 100 mg of said ibudilast.

Provided herein in another aspect is a pharmaceutical composition comprising about 3% w/w to about 15% w/w ibudilast, about 30% w/w to about 40% w/w lactose, about 30% w/w to about 40% w/w microcrystalline cellulose, about 15% w/w to about 25% w/w hypromellose, about 0.2% w/w to about 0.8% w/w magnesium stearate, and about 0.5% w/w to about 5% w/w colloidal silicon dioxide. In some embodiments, the lactose is lactose monohydrate. In some embodiments, the pharmaceutical composition comprises about 10% w/w ibudilast, about 35% w/w lactose monohydrate, about 33.5% w/w microcrystalline cellulose, about 20% w/w hypromellose, about 0.5% w/w magnesium stearate, and about 1% w/w colloidal silicon dioxide. In some embodiments, the composition is in the form of a tablet. In some embodiments, the tablet has a coating. In some embodiments, the coating comprises polyvinyl alcohol, plasticizer, and pigment. In some embodiments, the coating comprises methacrylic acid and ethyl acrylate copolymer dispersion; triethyl citrate; and talc. In some embodiments, the composition is in the form of a capsule. In some embodiments, the composition is devoid of hydroxypropyl methylcellulose-phthalate. In some embodiments, the composition is devoid of hydrogenated castor oil.

DETAILED DESCRIPTION

The practice of the present disclosure will employ, unless otherwise indicated, conventional methods of chemistry, biochemistry, and pharmacology, within the skill of the art. Such techniques are explained fully in the literature. See, e.g., A. L. Lehninger, Biochemistry (Worth Publishers, Inc., current addition); Morrison and Boyd, Organic Chemistry (Allyn and Bacon, Inc., current addition); J. March, Advanced Organic Chemistry (McGraw Hill, current addition); Remington: The Science and Practice of Pharmacy, A. Gennaro, Ed., 20th Ed.; FDA's Orange Book, Goodman & Gilman The Pharmacological Basis of Therapeutics, J. Griffith Hardman, L. L. Limbird, A. Gilman, 11th Ed., 2005, The Merck Manual, 18th edition, 2007, and The Merck Manual of Medical Information 2003.

All publications cited herein, including internet articles, the FDA Orange Book (available on the FDA's website), books, handbooks, journal articles, patents and patent applications, whether supra or infra, are hereby incorporated by reference in their entirety.

Definitions

Before describing the present disclosure in detail, it is to be understood that this disclosure is not limited to particular administration modes, patient populations, and the like, as such may vary, as will be apparent from the accompanying description.

It must be noted that, as used in this specification and the intended claims, the singular forms "a," "an," and "the" include plural referents unless the context clearly dictates otherwise. Thus, for example, reference to "a drug" includes a single drug as well as two or more of the same or different drugs, reference to "an optional excipient" refers to a single optional excipient as well as two or more of the same or different optional excipients, and the like.

In describing and claiming the present disclosure, the following terminology will be used in accordance with the definitions described below.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention. When an embodiment is defined by one of these terms (e.g., "comprising") it should be understood that this disclosure also includes alternative embodiments, such as "consisting essentially of" and "consisting of" for said embodiment.

"Optional" or "optionally" means that the subsequently described circumstance may or may not occur, so that the description includes instances where the circumstance occurs and instances where it does not.

"Pharmaceutically acceptable excipient or carrier" refers to an excipient that may optionally be included in the compositions of the disclosure and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly salts containing pharmaceutically acceptable cations include, but are not limited to, sodium, potassium, calcium, aluminum, lithium, and ammonium (including substituted ammonium).

"Active molecule" or "active agent" as described herein includes any agent, drug, compound, composition of matter or mixture which provides some pharmacologic, often beneficial, effect that can be demonstrated in vivo or in vitro. This includes foods, food supplements, nutrients, nutraceuticals, drugs, vaccines, antibodies, vitamins, and other beneficial agents. As used herein, the terms further include any physiologically or pharmacologically active substance that produces a localized or systemic effect in a patient. In specific embodiments, the active molecule or active agent may include ibudilast or a pharmaceutically acceptable salt thereof.

"Substantially" or "essentially" means nearly totally or completely, for instance, 90% or 95% or greater of some given quantity.

The terms "subject," "individual" or "patient" are used interchangeably herein and refer to a vertebrate, preferably a mammal. Mammals include, but are not limited to, mice, rodents, rats, simians, humans, farm animals, dogs, cats, sport animals and pets. In some embodiments, subject, individual, or patient is in reference to a human.

The terms "pharmacologically effective amount" or "therapeutically effective amount" of a composition or agent, as provided herein, refer to a nontoxic but sufficient amount of the composition or agent to provide the desired response, such as a reduction or reversal of any disease or disorder described herein. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein.

The term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term. For example, in some embodiments, it will mean plus or minus 5% of the particular term. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number.

As used herein, the term "treatment" or "treating" means any treatment of a disease or condition or associated disorder, in a patient, including inhibiting the disease or condition, that is, arresting or suppressing the development of clinical symptoms. "Treatment" or "treating" also includes arresting the development of or reversing the symptom or symptoms of a disease. For purposes of the various aspects and embodiments of the present disclosure, beneficial or desired clinical results include, but are not limited to, reduction, alleviation, or amelioration of one or more manifestations of or negative effects of any disease or disorder described herein, improvement in one or more clinical outcomes, diminishment of extent of any disease or disorder described herein, delay or slowing of any disease or disorder described herein progression, amelioration, palliation, or stabilization of the any disease or disorder described herein state, and other beneficial results described herein.

In some aspects, the term "treating" refers to an improvement in clinical outcomes. The term "clinical outcome" refers to any clinical observation or measurement relating to a patient's reaction to a therapy.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

Described herein are high dosage forms of ibudilast, which include tablet and capsule forms. High dosage forms facilitate ease of administration and increase patient compliance. In some embodiments, the high dosage form is a tablet form or capsule form with a specific dissolution profile as described herein. In some embodiments, the high dosage form is a tablet form or capsule form with a specific component profile described herein.

Ibudilast

The methods of the disclosure are based upon administration of the molecule, ibudilast. Ibudilast is a small molecule drug (molecular weight of 230.3) having the structure shown below.

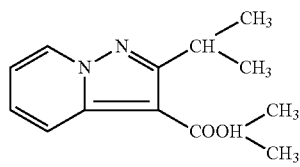

Ibudilast is also found under ChemBank ID 3227, CAS #50847-11-5, and Beilstein Handbook Reference No. 5-24-03-00396. Its molecular formula corresponds to $C_{14}H_{18}N_2O$. Ibudilast is also known by various chemical names including 2-methyl-1-(2-(1-methylethyl)pyrazolo(1,5-a)pyridin-3-yl)1-propanone; 3-isobutyryl-2-isopropylpyrazolo(1,5-a)pyridine; and 1-(2-isopropyl-pyrazolo[1,5-a]pyridin-3-yl)-2-methyl-propan-1-one. Other synonyms for ibudilast include Ibudilastum (Latin), BRN 0656579, KC-404, and MN-166. Its brand name is KETAS®. Ibudilast, as referred to herein, is meant to include any and all pharmaceutically acceptable salt forms thereof, prodrug forms (e.g., the corresponding ketal), solvates, and the like, as appropriate for use in its intended formulation for administration.

Ibudilast is an inhibitor of the macrophage inhibitory factor (MIF). Ibudilast is also a selective inhibitor of cyclic nucleotide phosphodiesterases (PDEs) 3A, 4, 10A1 and 11A1 (Gibson et al., Eur. J. Pharmacol. 538: 39-42, 2006), and has also been reported to have leukotriene D4 and PAF antagonistic activities. Its profile appears effectively anti-inflammatory and unique in comparison to other PDE inhibitors and anti-inflammatory agents. PDEs catalyze the hydrolysis of the phosphoester bond on the 3'-carbon to yield the corresponding 5'-nucleotide monophosphate. Thus, they regulate the cellular concentrations of cyclic nucleotides. Since extracellular receptors for many hormones and neurotransmitters utilize cyclic nucleotides as second messengers, the PDEs also regulate cellular responses to these extracellular signals. There are at least eight classes of PDEs: $Ca_2$+/calmodulin-dependent PDEs (PDE1); cGMP-stimulated PDEs (PDE2); cGMP-inhibited PDEs (PDE3); cAMP-specific PDEs (PDE4); cGMP-binding PDEs (PDES); photoreceptor PDEs (PDE6); high affinity, cAMP-specific PDEs (PDE7); and high affinity cGMP-specific PDEs (PDE9). Ibudilast acts to suppress inflammation via action on inflammatory cells (e.g., glial cells) resulting in the suppression of both pro-inflammatory mediator and neuroactive mediator release. Ibudilast may also suppress the production of pro-inflammatory cytokines (IL-1ß, TNF-α) and may enhance the production of the anti-inflammatory cytokines (IL-4, IL-10). References related to the foregoing include the following: Obernolte, R., et al. (1993) "The cDNA of a human lymphocyte cyclic-AMP phosphodiesterase (PDE IV) reveals a multigene family" Gene 129: 239-247; Rile, G., et al. (2001) "Potentiation of ibudilast inhibition of platelet aggregation in the presence of endothelial cells" Thromb. Res. 102: 239-246; Souness, J. E., et al. (1994) "Possible role of cyclic AMP phosphodiesterases in the actions of ibudilast on eosinophil thromboxane generation and airways smooth muscle tone" Br. J. Pharmacol. 111: 1081-1088; Suzumura, A., et al. (1999) "Ibudilast suppresses TNF-alpha production by glial cells functioning mainly as type III phosphodiesterase inhibitor in CNS" Brain Res. 837: 203-212; Takuma, K., et al. (2001) "Ibudilast attenuates astrocyte apoptosis via cyclic GMP signaling pathway in an in vitro reperfusion model" Br. J. Pharmacol.

133: 841-848. Ibudilast exhibits good CNS penetration; Sanftner et al. Xenobiotica, (2009) 39: 964-977.

As stated previously, a reference to any one or more of the herein-described drugs, in particular ibudilast, is meant to encompass, where applicable, any and all enantiomers, mixtures of enantiomers including racemic mixtures, prodrugs, pharmaceutically acceptable salt forms, hydrates (e.g., monohydrates, dihydrates, etc.), solvates, different physical forms (e.g., crystalline solids, amorphous solids), metabolites, and the like.

Component Profiles

In one aspect is a pharmaceutical composition comprising, consisting essentially of, or consisting of about 3% w/w to about 15% w/w ibudilast, about 30% w/w to about 40% w/w lactose, about 30% w/w to about 40% w/w microcrystalline cellulose, about 15% w/w to about 25% w/w hypromellose, about 0.2% w/w to about 0.8% w/w magnesium stearate, and about 0.5% w/w to about 5% w/w colloidal silicon dioxide. In some embodiments, the pharmaceutical composition comprises, consists essentially of, or consists of about 5% w/w to about 15% w/w ibudilast, about 30% w/w to about 40% w/w lactose, about 30% w/w to about 35% w/w microcrystalline cellulose, about 15% w/w to about 25% w/w hypromellose, about 0.2% w/w to about 0.8% w/w magnesium stearate, and about 0.5% w/w to about 5% w/w colloidal silicon dioxide.

In some embodiments, the pharmaceutical composition comprises, consists essentially of, or consists of about 10% w/w ibudilast, about 35% w/w lactose monohydrate, about 33.5% w/w microcrystalline cellulose, about 20% w/w hypromellose, about 0.5% w/w magnesium stearate, and about 1% w/w colloidal silicon dioxide. In some embodiments, the pharmaceutical composition comprises, consists essentially of, or consists of about 5% w/w ibudilast, about 37% w/w lactose, about 38.5% w/w microcrystalline cellulose, about 18% w/w hypromellose, about 0.5% w/w magnesium stearate, and about 1% w/w colloidal silicon dioxide. In some embodiments, the pharmaceutical composition comprises, consists essentially of, or consists of about 10% w/w ibudilast, about 35% w/w lactose, about 33.5% w/w microcrystalline cellulose, about 20% w/w hypromellose, about 0.5% w/w magnesium stearate, and about 1% w/w colloidal silicon dioxide. In some embodiments, the lactose is lactose monohydrate.

In some embodiments, the pharmaceutical composition comprises about 1% w/w to about 20% w/w ibudilast, about 1% w/w to about 25% w/w ibudilast, about 1% w/w to about 30% w/w ibudilast, about 1% w/w to about 35% w/w ibudilast, about 1% w/w to about 40% w/w ibudilast, about 1% w/w to about 45% w/w ibudilast, about 1% w/w to about 50% w/w ibudilast, about 3% w/w to about 20% w/w ibudilast, about 3% w/w to about 25% w/w ibudilast, about 3% w/w to about 30% w/w ibudilast, about 3% w/w to about 35% w/w ibudilast, about 3% w/w to about 40% w/w ibudilast, about 3% w/w to about 45% w/w ibudilast, about 3% w/w to about 50% w/w ibudilast, about 5% w/w to about 10% w/w ibudilast, about 5% w/w to about 15% w/w ibudilast, about 5% w/w to about 20% w/w ibudilast, about 5% w/w to about 25% w/w ibudilast, about 5% w/w to about 30% w/w ibudilast, about 5% w/w to about 35% w/w ibudilast, about 5% w/w to about 40% w/w ibudilast, about 5% w/w to about 45% w/w ibudilast, about 5% w/w to about 50% w/w ibudilast, about 10% w/w to about 15% w/w ibudilast, about 10% w/w to about 20% w/w ibudilast, about 10% w/w to about 25% w/w ibudilast, about 10% w/w to about 30% w/w ibudilast, about 10% w/w to about 35% w/w ibudilast, about 10% w/w to about 40% w/w ibudilast, about 10% w/w to about 45% w/w ibudilast, or about 10% w/w to about 50% w/w ibudilast. In some embodiments, the pharmaceutical composition comprises about 5% w/w to about 15% w/w ibudilast.

In some embodiments, the pharmaceutical composition comprises about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w, about 25% w/w, about 26% w/w, about 27% w/w, about 28% w/w, about 29% w/w, about 30% w/w, about 31% w/w, about 32% w/w, about 33% w/w, about 34% w/w, about 35% w/w, about 36% w/w, about 37% w/w, about 38% w/w, about 39% w/w, about 40% w/w, about 41% w/w, about 42% w/w, about 43% w/w, about 44% w/w, about 45% w/w, about 46% w/w, about 47% w/w, about 48% w/w, about 49% w/w, or about 50% w/w ibudilast. In some embodiments, the pharmaceutical composition comprises about 10% w/w ibudilast. In some embodiments, the pharmaceutical composition comprises about 5% w/w ibudilast.

In one aspect is a pharmaceutical composition comprising about 15% w/w to about 20% w/w lactose, about 15% w/w to about 25% w/w lactose, about 15% w/w to about 30% w/w lactose, about 15% w/w to about 35% w/w lactose, about 15% w/w to about 40% w/w lactose, about 15% w/w to about 45% w/w lactose, about 15% w/w to about 50% w/w lactose, about 15% w/w to about 55% w/w lactose, about 15% w/w to about 60% w/w lactose, about 20% w/w to about 25% w/w lactose, about 20% w/w to about 30% w/w lactose, about 20% w/w to about 35% w/w lactose, about 20% w/w to about 40% w/w lactose, about 20% w/w to about 45% w/w lactose, about 20% w/w to about 50% w/w lactose, about 20% w/w to about 55% w/w lactose, about 20% w/w to about 60% w/w lactose, about 25% w/w to about 30% w/w lactose, about 25% w/w to about 35% w/w lactose, about 25% w/w to about 40% w/w lactose, about 25% w/w to about 45% w/w lactose, about 25% w/w to about 50% w/w lactose, about 25% w/w to about 55% w/w lactose, about 25% w/w to about 60% w/w lactose, about 30% w/w to about 35% w/w lactose, about 30% w/w to about 40% w/w lactose, about 30% w/w to about 45% w/w lactose, about 30% w/w to about 50% w/w lactose, about 30% w/w to about 55% w/w lactose, about 30% w/w to about 60% w/w lactose, about 35% w/w to about 40% w/w lactose, about 35% w/w to about 45% w/w lactose, about 35% w/w to about 50% w/w lactose, about 35% w/w to about 55% w/w lactose, or about 35% w/w to about 60% w/w lactose. In some embodiments, the pharmaceutical composition comprises about 30% w/w to about 40% w/w lactose.

In some embodiments, the pharmaceutical composition comprises about 15% w/w, about 16% w/w, about 17% w/w, about 18% w/w, about 19% w/w, about 20% w/w, about 21% w/w, about 22% w/w, about 23% w/w, about 24% w/w, about 25% w/w, about 26% w/w, about 27% w/w, about 28% w/w, about 29% w/w, about 30% w/w, about 31% w/w, about 32% w/w, about 33% w/w, about 34% w/w, about 35% w/w, about 36% w/w, about 37% w/w, about 38% w/w, about 39% w/w, about 40% w/w, about 41% w/w, about 42% w/w, about 43% w/w, about 44% w/w, about 45% w/w, about 46% w/w, about 47% w/w, about 48% w/w, about 49% w/w, about 50% w/w, about 51% w/w, about 52% w/w, about 53% w/w, about 54% w/w, about 55% w/w, about 56% w/w, about 57% w/w, about 58% w/w, about 59% w/w, or about 60% w/w lactose. In some embodiments, the pharmaceutical composition comprises about 35% w/w lactose. In some embodiments, the pharmaceutical composition comprises about 37% w/w lactose.

In one aspect is a pharmaceutical composition comprising about 15% w/w to about 20% w/w lactose monohydrate, about 15% w/w to about 25% w/w lactose monohydrate, about 15% w/w to about 30% w/w lactose monohydrate, about 15% w/w to about 35% w/w lactose monohydrate, about 15% w/w to about 40% w/w lactose monohydrate, about 15% w/w to about 45% w/w lactose monohydrate, about 15% w/w to about 50% w/w lactose monohydrate, about 15% w/w to about 55% w/w lactose monohydrate, about 15% w/w to about 60% w/w lactose monohydrate, about 20% w/w to about 25% w/w lactose monohydrate, about 20% w/w to about 30% w/w lactose monohydrate, about 20% w/w to about 35% w/w lactose monohydrate, about 20% w/w to about 40% w/w lactose monohydrate, about 20% w/w to about 45% w/w lactose monohydrate, about 20% w/w to about 50% w/w lactose monohydrate, about 20% w/w to about 55% w/w lactose monohydrate, about 20% w/w to about 60% w/w lactose monohydrate about 25% w/w to about 30% w/w lactose monohydrate, about 25% w/w to about 35% w/w lactose monohydrate, about 25% w/w to about 40% w/w lactose monohydrate, about 25% w/w to about 45% w/w lactose monohydrate, about 25% w/w to about 50% w/w lactose monohydrate, about 25% w/w to about 55% w/w lactose monohydrate, about 25% w/w to about 60% w/w lactose monohydrate, about 30% w/w to about 35% w/w lactose monohydrate, about 30% w/w to about 40% w/w lactose monohydrate, about 30% w/w to about 45% w/w lactose monohydrate, about 30% w/w to about 50% w/w lactose monohydrate, about 30% w/w to about 55% w/w lactose monohydrate, about 30% w/w to about 60% w/w lactose monohydrate, about 35% w/w to about 40% w/w lactose monohydrate, about 35% w/w to about 45% w/w lactose monohydrate, about 35% w/w to about 50% w/w lactose monohydrate, about 35% w/w to about 55% w/w lactose monohydrate, or about 35% w/w to about 60% w/w lactose monohydrate. In some embodiments, the pharmaceutical composition comprises about 30% w/w to about 40% w/w lactose monohydrate.

In some embodiments, the pharmaceutical composition comprises about 15% w/w, about 16% w/w, about 17% w/w, about 18% w/w, about 19% w/w, about 20% w/w, about 21% w/w, about 22% w/w, about 23% w/w, about 24% w/w, about 25% w/w, about 26% w/w, about 27% w/w, about 28% w/w, about 29% w/w, about 30% w/w, about 31% w/w, about 32% w/w, about 33% w/w, about 34% w/w, about 35% w/w, about 36% w/w, about 37% w/w, about 38% w/w, about 39% w/w, about 40% w/w, about 41% w/w, about 42% w/w, about 43% w/w, about 44% w/w, about 45% w/w, about 46% w/w, about 47% w/w, about 48% w/w, about 49% w/w, about 50% w/w, about 51% w/w, about 52% w/w, about 53% w/w, about 54% w/w, about 55% w/w, about 56% w/w, about 57% w/w, about 58% w/w, about 59% w/w, or about 60% w/w lactose monohydrate. In some embodiments, the pharmaceutical composition comprises about 35% w/w lactose monohydrate. In some embodiments, the pharmaceutical composition comprises about 37% w/w lactose monohydrate.

In one aspect is a pharmaceutical composition comprising about 15% w/w to about 20% w/w microcrystalline cellulose, about 15% w/w to about 25% w/w microcrystalline cellulose, about 15% w/w to about 30% w/w microcrystalline cellulose, about 15% w/w to about 35% w/w microcrystalline cellulose, about 15% w/w to about 40% w/w microcrystalline cellulose, about 15% w/w to about 45% w/w microcrystalline cellulose, about 15% w/w to about 50% w/w microcrystalline cellulose, about 15% w/w to about 55% w/w microcrystalline cellulose, about 15% w/w to about 60% w/w microcrystalline cellulose, about 20% w/w to about 25% w/w microcrystalline cellulose, about 20% w/w to about 30% w/w microcrystalline cellulose, about 20% w/w to about 35% w/w microcrystalline cellulose, about 20% w/w to about 40% w/w microcrystalline cellulose, about 20% w/w to about 45% w/w microcrystalline cellulose, about 20% w/w to about 50% w/w microcrystalline cellulose, about 20% w/w to about 55% w/w microcrystalline cellulose, about 20% w/w to about 60% w/w microcrystalline cellulose about 25% w/w to about 30% w/w microcrystalline cellulose, about 25% w/w to about 35% w/w microcrystalline cellulose, about 25% w/w to about 40% w/w microcrystalline cellulose, about 25% w/w to about 45% w/w microcrystalline cellulose, about 25% w/w to about 50% w/w microcrystalline cellulose, about 25% w/w to about 55% w/w microcrystalline cellulose, about 25% w/w to about 60% w/w microcrystalline cellulose, about 30% w/w to about 35% w/w microcrystalline cellulose, about 30% w/w to about 40% w/w microcrystalline cellulose, about 30% w/w to about 45% w/w microcrystalline cellulose, about 30% w/w to about 50% w/w microcrystalline cellulose, about 30% w/w to about 55% w/w microcrystalline cellulose, about 30% w/w to about 60% w/w microcrystalline cellulose, about 35% w/w to about 40% w/w microcrystalline cellulose, about 35% w/w to about 45% w/w microcrystalline cellulose, about 35% w/w to about 50% w/w microcrystalline cellulose, about 35% w/w to about 55% w/w microcrystalline cellulose, or about 35% w/w to about 60% w/w microcrystalline cellulose. In some embodiments, the pharmaceutical composition comprises about 30% w/w to about 35% w/w microcrystalline cellulose. In some embodiments, the pharmaceutical composition comprises about 30% w/w to about 38.5% w/w microcrystalline cellulose.

In some embodiments, the pharmaceutical composition comprises about 15% w/w, about 16% w/w, about 17% w/w, about 18% w/w, about 19% w/w, about 20% w/w, about 21% w/w, about 22% w/w, about 23% w/w, about 24% w/w, about 25% w/w, about 26% w/w, about 27% w/w, about 28% w/w, about 29% w/w, about 30% w/w, about 30.5% w/w, about 31% w/w, about 31.5% w/w, about 32% w/w, about 32.5% w/w, about 33% w/w, about 33.5% w/w, about 34% w/w, about 34.5% w/w, about 35% w/w, about 35.5% w/w, about 36% w/w, about 36.5% w/w, about 37% w/w, about 37.5% w/w, about 38% w/w, about 38.5% w/w, about 39% w/w, about 39.5% w/w, about 40% w/w, about 41% w/w, about 42% w/w, about 43% w/w, about 44% w/w, about 45% w/w, about 46% w/w, about 47% w/w, about 48% w/w, about 49% w/w, about 50% w/w, about 51% w/w, about 52% w/w, about 53% w/w, about 54% w/w, about 55% w/w, about 56% w/w, about 57% w/w, about 58% w/w, about 59% w/w, or about 60% w/w microcrystalline cellulose. In some embodiments, the pharmaceutical composition comprises about 33.5% w/w microcrystalline cellulose. In some embodiments, the pharmaceutical composition comprises about 38.5% w/w microcrystalline cellulose.

In one aspect is a pharmaceutical composition comprising about 15% w/w to about 20% w/w hypromellose, about 15% w/w to about 25% w/w hypromellose, about 15% w/w to about 30% w/w hypromellose, about 15% w/w to about 35% w/w hypromellose, about 15% w/w to about 40% w/w hypromellose, about 15% w/w to about 45% w/w hypromellose, about 15% w/w to about 50% w/w hypromellose, about 15% w/w to about 55% w/w hypromellose, about 15% w/w to about 60% w/w hypromellose, about 20% w/w to about 25% w/w hypromellose, about 20% w/w to about 30% w/w hypromellose, about 20% w/w to about 35% w/w hypromellose, about 20% w/w to about 40% w/w hypromellose, about 20% w/w to about 45% w/w hypromellose, about 20% w/w to about 50% w/w hypromellose, about 20% w/w to about 55% w/w hypromellose, about 20% w/w to about 60% w/w hypromellose about 25% w/w to about 30% w/w hypromellose, about 25% w/w to about 35% w/w hypromellose, about 25% w/w to about 40% w/w hypromellose, about 25% w/w to about 45% w/w hypromellose, about 25% w/w to about 50% w/w hypromellose, about 25% w/w to about 55% w/w hypromellose, about 25% w/w to about 60% w/w hypromellose, about 30% w/w to about 35% w/w hypromellose, about 30% w/w to about 40% w/w hypromellose, about 30% w/w to about 45% w/w hypromellose, about 30% w/w to about 50% w/w hypromellose, about 30% w/w to about 55% w/w hypromellose, about 30% w/w to about 60% w/w hypromellose, about 35% w/w to about 40% w/w hypromellose, about 35% w/w to about 45% w/w hypromellose, about 35% w/w to about 50% w/w hypromellose, about 35% w/w to about 55% w/w hypromellose, or about 35% w/w to about 60% w/w hypromellose. In some embodiments, the pharmaceutical composition comprises about 15% w/w to about 25% w/w hypromellose.

In some embodiments, the pharmaceutical composition comprises about 15% w/w, about 16% w/w, about 17% w/w, about 18% w/w, about 19% w/w, about 20% w/w, about 21% w/w, about 22% w/w, about 23% w/w, about 24% w/w, about 25% w/w, about 26% w/w, about 27% w/w, about 28% w/w, about 29% w/w, about 30% w/w, about 30.5% w/w, about 31% w/w, about 31.5% w/w, about 32% w/w, about 32.5% w/w, about 33% w/w, about 34% w/w, about 35% w/w, about 36% w/w, about 37% w/w, about 38% w/w, about 39% w/w, w/w, about 40% w/w, about 41% w/w, about 42% w/w, about 43% w/w, about 44% w/w, about 45% w/w, about 46% w/w, about 47% w/w, about 48% w/w, about 49% w/w, about 50% w/w, about 51% w/w, about 52% w/w, about 53% w/w, about 54% w/w, about 55% w/w, about 56% w/w, about 57% w/w, about 58% w/w, about 59% w/w, or about 60% w/w hypromellose. In some embodiments, the pharmaceutical composition comprises about 20% w/w hypromellose. In some embodiments, the pharmaceutical composition comprises about 18% w/w hypromellose.

In one aspect is a pharmaceutical composition comprising about 0.1% w/w to about 0.3% w/w magnesium stearate, about 0.1% w/w to about 0.4% w/w magnesium stearate, about 0.1% w/w to about 0.5% w/w magnesium stearate, about 0.1% w/w to about 0.6% w/w magnesium stearate, about 0.1% w/w to about 0.7% w/w magnesium stearate, about 0.1% w/w to about 0.8% w/w magnesium stearate, about 0.1% w/w to about 0.9% w/w magnesium stearate, about 0.1% w/w to about 1.0% w/w magnesium stearate, about 0.1% w/w to about 1.5% w/w magnesium stearate, about 0.1% w/w to about 2.0% w/w magnesium stearate, about 0.1% w/w to about 2.5% w/w magnesium stearate, about 0.1% w/w to about 3.0% w/w magnesium stearate, about 0.1% w/w to about 3.5% w/w magnesium stearate, about 0.1% w/w to about 4.0% w/w magnesium stearate, about 0.1% w/w to about 4.5% w/w magnesium stearate, about 0.1% w/w to about 5.0% w/w magnesium stearate, about 0.2% w/w to about 0.3% w/w magnesium stearate, about 0.2% w/w to about 0.4% w/w magnesium stearate, about 0.2% w/w to about 0.5% w/w magnesium stearate, about 0.2% w/w to about 0.6% w/w magnesium stearate, about 0.2% w/w to about 0.7% w/w magnesium stearate, about 0.2% w/w to about 0.8% w/w magnesium stearate, about 0.2% w/w to about 0.9% w/w magnesium stearate, about 0.2% w/w to about 1.0% w/w magnesium stearate, about 0.2% w/w to about 1.5% w/w magnesium stearate, about 0.2% w/w to about 2.0% w/w magnesium stearate, about 0.2% w/w to about 2.5% w/w magnesium stearate, about 0.2% w/w to about 3.0% w/w magnesium stearate, about 0.2% w/w to about 3.5% w/w magnesium stearate, about 0.2% w/w to about 4.0% w/w magnesium stearate, about 0.2% w/w to about 4.5% w/w magnesium stearate, or about 0.2% w/w to about 5.0% w/w magnesium stearate. In some embodiments, the pharmaceutical composition comprises about 0.2% w/w to about 0.8% w/w magnesium stearate.

In some embodiments, the pharmaceutical composition comprises about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1.0% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2.0% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3.0% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4.0% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, or about 5.0% magnesium stearate. In some embodiments, the pharmaceutical composition comprises about 0.5% w/w magnesium stearate.

In another aspect is a pharmaceutical composition comprising about 0.1% w/w to about 0.3% w/w colloidal silicon dioxide, about 0.1% w/w to about 0.2% w/w colloidal silicon dioxide, about 0.1% w/w to about 0.4% w/w colloidal silicon dioxide, about 0.1% w/w to about 0.5% w/w colloidal silicon dioxide, about 0.1% w/w to about 0.6% w/w colloidal silicon dioxide, about 0.1% w/w to about 0.7% w/w colloidal silicon dioxide, about 0.1% w/w to about 0.8% w/w colloidal silicon dioxide, about 0.1% w/w to about 0.9% w/w colloidal silicon dioxide, about 0.1% w/w to about 1.0% w/w colloidal silicon dioxide, about 0.1% w/w to about 1.5% w/w colloidal silicon dioxide, about 0.1% w/w to about 2.0% w/w colloidal silicon dioxide, about 0.1% w/w to about 2.5% w/w colloidal silicon dioxide, about 0.1% w/w to about 3.0% w/w colloidal silicon dioxide, about 0.1% w/w to about 3.5% w/w colloidal silicon dioxide, about 0.1% w/w to about 4.0% w/w colloidal silicon dioxide, about 0.1% w/w to about 4.5% w/w colloidal silicon dioxide, about 0.1% w/w to about 5.0% w/w colloidal silicon dioxide, about 0.1% w/w to about 10.0% w/w colloidal silicon dioxide, about 0.1% w/w to about 15.0% w/w colloidal silicon dioxide, about 0.1% w/w to about 20.0% w/w colloidal silicon dioxide, about 0.2% w/w to about 0.3% w/w colloidal silicon dioxide, about 0.2% w/w to about 0.4% w/w colloidal silicon dioxide, about 0.2% w/w to about 0.5% w/w colloidal silicon dioxide, about 0.2% w/w to about 0.6% w/w colloidal silicon dioxide, about 0.2% w/w to about 0.7% w/w colloidal silicon dioxide, about 0.2% w/w to about 0.8% w/w colloidal silicon dioxide, about 0.2% w/w to about 0.9% w/w colloidal silicon dioxide, about 0.2% w/w to about 1.0% w/w colloidal silicon dioxide, about 0.2% w/w to about 1.5% w/w colloidal silicon dioxide, about 0.2% w/w to about 2.0% w/w colloidal silicon dioxide, about 0.2% w/w to about 2.5% w/w colloidal silicon dioxide, about 0.2% w/w to about 3.0% w/w colloidal silicon dioxide, about 0.2% w/w to about 3.5% w/w colloidal silicon dioxide, about 0.2% w/w to about 4.0% w/w colloidal silicon dioxide, about 0.2% w/w to about 4.5% w/w colloidal silicon dioxide, or about 0.2% w/w to about 5.0% w/w colloidal silicon dioxide, about 0.2% w/w to about 10.0% w/w colloidal silicon dioxide, about 0.2% w/w to about 15.0% w/w colloidal silicon dioxide, about 0.2% w/w to about 20.0% w/w colloidal silicon dioxide, about 0.3% w/w to about 0.4% w/w colloidal silicon dioxide, about 0.3% w/w to about 0.5% w/w colloidal silicon dioxide, about 0.3% w/w to about 0.6% w/w colloidal silicon dioxide, about 0.3% w/w to about 0.7% w/w colloidal silicon dioxide, about 0.3% w/w to about 0.8% w/w colloidal silicon dioxide, about 0.3% w/w to about 0.9% w/w colloidal silicon dioxide, about 0.3% w/w to about 1.0% w/w colloidal silicon dioxide, about 0.3% w/w to about 1.5% w/w colloidal silicon dioxide, about 0.3% w/w to about 2.0% w/w colloidal silicon dioxide, about 0.3% w/w to about 2.5% w/w colloidal silicon dioxide, about 0.3% w/w to about 3.0% w/w colloidal silicon dioxide, about 0.3% w/w to about 3.5% w/w colloidal silicon dioxide, about 0.3% w/w to about 4.0% w/w colloidal silicon dioxide, about 0.3% w/w to about 4.5% w/w colloidal silicon dioxide, or about 0.3% w/w to about 5.0% w/w colloidal silicon dioxide, about 0.3% w/w to about 10.0% w/w colloidal silicon dioxide, about 0.3% w/w to about 15.0% w/w colloidal silicon dioxide, about 0.3% w/w to about 20.0% w/w colloidal silicon dioxide, about 0.4% w/w to about 0.5% w/w colloidal silicon dioxide, about 0.4% w/w to about 0.6% w/w colloidal silicon dioxide, about 0.4% w/w to about 0.7% w/w colloidal silicon dioxide, about 0.4% w/w to about 0.3% w/w colloidal silicon dioxide, about 0.4% w/w to about 0.9% w/w colloidal silicon dioxide, about 0.4% w/w to about 1.0% w/w colloidal silicon dioxide, about 0.4% w/w to about 1.5% w/w colloidal silicon dioxide, about 0.4% w/w to about 2.0% w/w colloidal silicon dioxide, about 0.4% w/w to about 2.5% w/w colloidal silicon dioxide, about 0.4% w/w to about 3.0% w/w colloidal silicon dioxide, about 0.4% w/w to about 3.5% w/w colloidal silicon dioxide, about 0.4% w/w to about 4.0% w/w colloidal silicon dioxide, about 0.4% w/w to about 4.5% w/w colloidal silicon dioxide, about 0.4% w/w to about 5.0% w/w colloidal silicon dioxide, about 0.4% w/w to about 10.0% w/w colloidal silicon dioxide, about 0.4% w/w to about 15.0% w/w colloidal silicon dioxide, about 0.4% w/w to about 20.0% w/w colloidal silicon dioxide, about 0.5% w/w to about 0.6% w/w colloidal silicon dioxide, about 0.5% w/w to about 0.7% w/w colloidal silicon dioxide, about 0.5% w/w to about 0.3% w/w colloidal silicon dioxide, about 0.5% w/w to about 0.9% w/w colloidal silicon dioxide, about 0.5% w/w to about 1.0% w/w colloidal silicon dioxide, about 0.5% w/w to about 1.5% w/w colloidal silicon dioxide, about 0.5% w/w to about 2.0% w/w colloidal silicon dioxide, about 0.5% w/w to about 2.5% w/w colloidal silicon dioxide, about 0.5% w/w to about 3.0% w/w colloidal silicon dioxide, about 0.5% w/w to about 3.5% w/w colloidal silicon dioxide, about 0.5% w/w to about 4.0% w/w colloidal silicon dioxide, about 0.5% w/w to about 4.5% w/w colloidal silicon dioxide, about 0.5% w/w to about 5.0% w/w colloidal silicon dioxide, about 0.5% w/w to about 10.0% w/w colloidal silicon dioxide, about 0.5% w/w to about 15.0% w/w colloidal silicon dioxide, or about 0.5% w/w to about 20.0% w/w colloidal silicon dioxide. In some embodiments, the pharmaceutical composition comprises about 0.5% w/w to about 5% w/w colloidal silicon dioxide.

In some embodiments, the pharmaceutical composition comprises about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1.0% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, w/w, about 2.0% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3.0% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4.0% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5.0% w/w colloidal silicon dioxide, about 10% w/w colloidal silicon dioxide, about 15% w/w colloidal silicon dioxide, about 20% w/w colloidal silicon dioxide. In some embodiments, the pharmaceutical composition comprises about 1.0% w/w colloidal silicon dioxide.

In some embodiments, the composition is in the form of a capsule. In some embodiments, the composition is in the form of a tablet. In some embodiments, the tablet has a coating. In some embodiments, the coating comprises polyvinyl alcohol, plasticizer, pigment, or any combination thereof. In some embodiments, the coating comprises polyvinyl alcohol, plasticizer, and pigment. In some embodiments, the coating comprises polyvinyl alcohol. In some embodiments, the coating comprises plasticizer. In some embodiments, the coating comprises pigment. In some embodiments, the coating comprises methacrylic acid and ethyl acrylate copolymer dispersion; triethyl citrate; talc; or any combination thereof. In some embodiments, the coating comprises methacrylic acid and ethyl acrylate copolymer dispersion; triethyl citrate; and talc. In some embodiments, the coating comprises methacrylic acid and ethyl acrylate copolymer dispersion. In some embodiments, the coating comprises triethyl citrate. In some embodiments, the coating comprises talc.

In some embodiments, the composition is devoid of hydroxypropyl methylcellulose-phthalate and hydrogenated castor oil. In some embodiments, the composition is devoid of hydroxypropyl methylcellulose-phthalate. In some embodiments, the composition is devoid of hydrogenated castor oil.

Dissolution Profiles

In one aspect is a pharmaceutical composition comprising, consisting essentially of, or consisting of ibudilast and at least one pharmaceutically acceptable excipient, wherein said composition has a dissolution profile wherein at least about 12% of said ibudilast has been released from said composition at about 2 hours when tested in USP Apparatus Type II at 50 rpm in 900 mL of simulated gastric fluid medium at 37° C. In some embodiments, provided herein is a pharmaceutical composition comprising, consisting essentially of, or consisting of ibudilast and at least one pharmaceutically acceptable excipient, wherein said pharmaceutical composition is in the form of a tablet or a capsule, and wherein said tablet or said capsule has a dissolution profile wherein at least about 12% of said ibudilast has been released from said tablet or said capsule at about 2 hours when tested in USP Apparatus Type II at 50 rpm in 900 mL of simulated gastric fluid medium at 37° C. In some embodiments, simulated gastric fluid medium is prepared by adding 20 g sodium chloride and 70 mL hydrochloric acid (37% w/w) in 10 L water, and adjusting to a pH of 1.2 using additional hydrochloric acid as necessary.

In some embodiments, at least about 8%, at least about 9%, at least about 10%, at least about 11%, at least about 12%, at least about 13%, at least about 14%, at least about 15%, at least about 16%, at least about 17%, at least about 18%, or at least about 19%, but no more than 20% of the ibudilast has been released from the composition or from the tablet or the capsule at about 2 hours when tested in USP Apparatus Type II at 50 rpm in 900 mL of simulated gastric fluid medium at 37° C.

In some embodiments, from about 8% to about 10%, from about 8% to about 12%, from about 8% to about 15%, from about 8% to about 18%, from about 8% to about 20%, from about 10% to about 13%, from about 10% to about 15%, or from about 10% to about 20% of the ibudilast has been released from the composition or from the tablet or the capsule at about 2 hours when tested in USP Apparatus Type II at 50 rpm in 900 mL of simulated gastric fluid medium at 37° C.

In some embodiments, about 8%, about 9%, about 10%, about 11%, about 12%, about 13%, about 14%, about 15%, about 16%, about 17%, about 18%, about 19%, or about 20% of the ibudilast has been released from the composition or from the tablet or the capsule at about 2 hours when tested in USP Apparatus Type II at 50 rpm in 900 mL of simulated gastric fluid medium at 37° C.

In some embodiments, the tablet has a coating comprising, consisting essentially of, or consisting of polyvinyl alcohol, plasticizer, pigment, or any combination thereof. In some embodiments, the tablet has a coating comprising, consisting essentially of, or consisting of polyvinyl alcohol, plasticizer, and pigment. In some embodiments, the tablet has a coating comprising polyvinyl alcohol. In some embodiments, the tablet has a coating comprising plasticizer. In some embodiments, the tablet has a coating comprising pigment.

In some embodiments, at least one pharmaceutically acceptable excipient comprises, consists essentially of, or consists of lactose monohydrate, microcrystalline cellulose, or hypromellose, or any combination of two or more thereof.

In some embodiments, the composition or the tablet or the capsule has a dissolution profile wherein at least about 25% of said ibudilast has been released from the composition or from the tablet or the capsule at about 4 hours when tested in USP Apparatus Type II at (a) 50 rpm in 900 mL of simulated gastric fluid medium at 37° C. for 2 hours, followed by (b) 50 rpm in 900 mL of phosphate buffer with 0.3% w/w sodium lauryl sulfate at a pH of 6.8 at 37° C. for another 2 hours.

In some embodiments, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, or at least about 39% but no more than 40% of the ibudilast has been released from the composition or from the tablet or the capsule at about 4 hours when tested in USP Apparatus Type II at (a) 50 rpm in 900 mL of simulated gastric fluid medium at 37° C. for 2 hours, followed by (b) 50 rpm in 900 mL of phosphate buffer with 0.3% w/w sodium lauryl sulfate at a pH of 6.8 at 37° C. for another 2 hours.

In some embodiments, from about 25% to about 30%, from about 25% to 35%, from about 25% to about 40%, from about 28% to about 30%, from about 28% to about 35%, from about 28% to about 40%, from about 30% to about 35%, or from about 30% to about 40% of the ibudilast has been released from the composition or from the tablet or the capsule at about 4 hours when tested in USP Apparatus Type II at (a) 50 rpm in 900 mL of simulated gastric fluid medium at 37° C. for 2 hours, followed by (b) 50 rpm in 900 mL of phosphate buffer with 0.3% w/w sodium lauryl sulfate at a pH of 6.8 at 37° C. for another 2 hours.

In some embodiments, about 25%, about 26%, about 27%, about 28%, about 29%, about 30%, about 31%, about 32%, about 33%, about 34%, about 35%, about 36%, about 37%, about 38%, about 39%, or about 40% of the ibudilast has been released from the composition or from the tablet or the capsule at about 4 hours when tested in USP Apparatus Type II at (a) 50 rpm in 900 mL of simulated gastric fluid medium at 37° C. for 2 hours, followed by (b) 50 rpm in 900 mL of phosphate buffer with 0.3% w/w sodium lauryl sulfate at a pH of 6.8 at 37° C. for another 2 hours.

In some embodiments, the composition or the tablet or the capsule has a dissolution profile wherein at least about 60% of said ibudilast has been released from the composition or from the tablet or the capsule at about 12 hours when tested in USP Apparatus Type II at (a) 50 rpm in 900 mL of simulated gastric fluid medium at 37° C. for 2 hours, followed by (b) 50 rpm in 900 mL of phosphate buffer with 0.3% w/w sodium lauryl sulfate at a pH of 6.8 at 37° C. for another 10 hours.

In some embodiments, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, or at least about 79%, but no more than 80% of the ibudilast has been released from the composition or from the tablet or the capsule at about 12 hours when tested in USP Apparatus Type II at (a) 50 rpm in 900 mL of simulated gastric fluid medium at 37° C. for 2 hours, followed by (b) 50 rpm in 900 mL of phosphate buffer with 0.3% w/w sodium lauryl sulfate at a pH of 6.8 at 37° C. for another 10 hours.

In some embodiments, from about 60% to about 65%, from about 60% to about 70%, from about 60% to about 75%, from about 60% to about 80%, from about 65% to about 70%, from about 65% to about 80%, from about 70% to about 75%, or from about 70% to about 80% of the ibudilast has been released from the composition or from the tablet or the capsule at about 12 hours when tested in USP Apparatus Type II at (a) 50 rpm in 900 mL of simulated gastric fluid medium at 37° C. for 2 hours, followed by (b) 50 rpm in 900 mL of phosphate buffer with 0.3% w/w sodium lauryl sulfate at a pH of 6.8 at 37° C. for another 10 hours.

In some embodiments, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, or about 88% of the ibudilast has been released from the composition or from the tablet or the capsule at about 12 hours when tested in USP Apparatus Type II at (a) 50 rpm in 900 mL of simulated gastric fluid medium at 37° C. for 2 hours, followed by (b) 50 rpm in 900 mL of phosphate buffer with 0.3% w/w sodium lauryl sulfate at a pH of 6.8 at 37° C. for another 10 hours.

In some embodiments, the composition or the tablet or the capsule has a dissolution profile wherein at least about 90% of said ibudilast has been released from the composition or from the tablet or the capsule at about 24 hours when tested in USP Apparatus Type II at (a) 50 rpm in 900 mL of simulated gastric fluid medium at 37° C. for 2 hours, followed by (b) 50 rpm in 900 mL of phosphate buffer with 0.3% w/w sodium lauryl sulfate at a pH of 6.8 at 37° C. for another 22 hours.

In some embodiments, at least about 90%, at least about 91%, at least about 92%, at least about 93%, at least about 94%, at least about 95%, at least about 96%, at least about 97%, at least about 98%, or at least about 99% of the ibudilast has been released from the composition or from the tablet or the capsule at about 24 hours when tested in USP Apparatus Type II at (a) 50 rpm in 900 mL of simulated gastric fluid medium at 37° C. for 2 hours, followed by (b) 50 rpm in 900 mL of phosphate buffer with 0.3% w/w sodium lauryl sulfate at a pH of 6.8 at 37° C. for another 22 hours.

In some embodiments, from about 90% to about 95%, or from about 90% to about 99% of the ibudilast has been released from the composition or from the tablet or the capsule at about 24 hours when tested in USP Apparatus Type II at (a) 50 rpm in 900 mL of simulated gastric fluid medium at 37° C. for 2 hours, followed by (b) 50 rpm in 900 mL of phosphate buffer with 0.3% w/w sodium lauryl sulfate at a pH of 6.8 at 37° C. for another 22 hours.

In some embodiments, about 90%, about 91%, about 92%, about 93%, about 94%, about 95%, about 96%, about 97%, about 98%, or about 99% of the ibudilast has been released from the composition or from the tablet or the capsule at about 24 hours when tested in USP Apparatus Type II at (a) 50 rpm in 900 mL of simulated gastric fluid medium at 37° C. for 2 hours, followed by (b) 50 rpm in 900 mL of phosphate buffer with 0.3% w/w sodium lauryl sulfate at a pH of 6.8 at 37° C. for another 22 hours.

In another aspect is a pharmaceutical composition comprising, consisting essentially of, or consisting of ibudilast and at least one pharmaceutically acceptable excipient, wherein said composition has a dissolution profile wherein no ibudilast has been released from said composition at about 2 hours when tested in USP Apparatus Type II at 50 rpm in 900 mL of simulated gastric fluid medium at 37° C. In some embodiments, provided herein is a pharmaceutical composition comprising, consisting essentially of, or consisting of ibudilast and at least one pharmaceutically acceptable excipient, wherein said pharmaceutical composition is in the form of a tablet or a capsule, and wherein said tablet or said capsule has a dissolution profile wherein no ibudilast has been released from said tablet or said capsule at about 2 hours when tested in USP Apparatus Type II at 50 rpm in 900 mL of simulated gastric fluid medium at 37° C.

In some embodiments, the composition or the tablet or the capsule exhibits an improved $C_{max}$ compared to an intermediate release formulation when administered to a human subject following a dosing protocol consisting of a three-day dose titration phase followed by an eleven-day multiple-dose phase, wherein said tablet or said capsule is administered as a 50-mg dose once daily during the three-day dose titration phase and said tablet or said capsule is administered as a 100-mg dose once daily during the eleven-day multiple-dose phase. In some embodiments, the composition or the tablet or the capsule exhibits an improved $C_{max}$ and a similar AUC compared to an intermediate release formulation when administered to a human subject following a dosing protocol consisting of a three-day dose titration phase followed by an eleven-day multiple-dose phase, wherein said tablet or said capsule is administered as a 50-mg dose once daily during the three-day dose titration phase and said tablet or said capsule is administered as a 100-mg dose once daily during the eleven-day multiple-dose phase.

In some embodiments, the tablet has a coating comprising, consisting essentially of, or consisting of methacrylic acid and ethyl acrylate copolymer dispersion; triethyl citrate; talc; or any combination thereof. In some embodiments, the coating comprises, consists essentially of, or consists of methacrylic acid and ethyl acrylate copolymer dispersion; triethyl citrate; and talc. In some embodiments, the coating comprises methacrylic acid and ethyl acrylate copolymer dispersion. In some embodiments, the coating comprises triethyl citrate. In some embodiments, the coating comprises talc.

In some embodiments, at least one pharmaceutically acceptable excipient comprises, consists essentially of, or consists of lactose monohydrate, microcrystalline cellulose, or hypromellose, or any combination of two or more thereof. In some embodiments, at least one pharmaceutically acceptable excipient comprises, consists essentially of, or consists of lactose monohydrate, microcrystalline cellulose, hypromellose, magnesium stearate, and colloidal silicon dioxide, or any combination of two or more thereof.

In some embodiments, the composition or the tablet or the capsule has a dissolution profile wherein about 10% to about 20% of said ibudilast has been released from said tablet at about 4 hours when tested in USP Apparatus Type II at (a) 50 rpm in 900 mL of simulated gastric fluid medium at 37° C. for 2 hours, followed by (b) 50 rpm in 900 mL of phosphate buffer with 0.3% w/w sodium lauryl sulfate at a pH of 6.8 at 37° C. for another 2 hours. In some embodiments, about 10%, about 11%, about 12%, about 13%, about 14%, about 15%, about 16%, about 17%, about 18%, about 19%, or about 20% of the ibudilast has been released from the composition or from the tablet or the capsule at about 4 hours when tested in USP Apparatus Type II at (a) 50 rpm in 900 mL of simulated gastric fluid medium at 37° C. for 2 hours, followed by (b) 50 rpm in 900 mL of phosphate buffer with 0.3% w/w sodium lauryl sulfate at a pH of 6.8 at 37° C. for another 2 hours.

In some embodiments, the composition or the tablet or the capsule has a dissolution profile wherein about 55% to about 65% of said ibudilast has been released from the composition or from the tablet or the capsule at about 12 hours when tested in USP Apparatus Type II at (a) 50 rpm in 900 mL of simulated gastric fluid medium at 37° C. for 2 hours, followed by (b) 50 rpm in 900 mL of phosphate buffer with 0.3% w/w sodium lauryl sulfate at a pH of 6.8 at 37° C. for another 10 hours. In some embodiments, about 55%, about 56%, about 57%, about 58%, about 59%, about 60%, about 61%, about 62%, about 63%, about 64%, or about 65% of the ibudilast has been released from the composition or from the tablet or the capsule at about 12 hours when tested in USP Apparatus Type II at (a) 50 rpm in 900 mL of simulated gastric fluid medium at 37° C. for 2 hours, followed by (b) 50 rpm in 900 mL of phosphate buffer with 0.3% w/w sodium lauryl sulfate at a pH of 6.8 at 37° C. for another 10 hours.

In some embodiments, the composition or the tablet or the capsule has a dissolution profile wherein about 85% to about 95% of said ibudilast has been released from the composition or from the tablet or the capsule at about 24 hours when tested in USP Apparatus Type II at (a) 50 rpm in 900 mL of simulated gastric fluid medium at 37° C. for 2 hours, followed by (b) 50 rpm in 900 mL of phosphate buffer with 0.3% w/w sodium lauryl sulfate at a pH of 6.8 at 37° C. for another 22 hours. In some embodiments, about 85%, about 86%, about 87%, about 88%, about 89%, about 90%, about 91%, about 92%, about 93%, about 94%, or about 95% of the ibudilast has been released from the composition or from the tablet or the capsule at about 24 hours when tested in USP Apparatus Type II at (a) 50 rpm in 900 mL of simulated gastric fluid medium at 37° C. for 2 hours, followed by (b) 50 rpm in 900 mL of phosphate buffer with 0.3% w/w sodium lauryl sulfate at a pH of 6.8 at 37° C. for another 22 hours.

In another aspect, provided herein is a method for extended release of ibudilast over a 24-hour period in a subject. In some embodiments, the method comprises administering to the subject a pharmaceutical composition comprising, consisting essentially of, or consisting of about 3% w/w to about 15% w/w ibudilast, about 30% w/w to about 40% w/w lactose, about 30% w/w to about 40% w/w microcrystalline cellulose, about 15% w/w to about 25% w/w hypromellose, about 0.2% w/w to about 0.8% w/w magnesium stearate, and about 0.5% w/w to about 5% w/w colloidal silicon dioxide. In some embodiments, the method comprises administering to the subject a pharmaceutical composition comprising, consisting essentially of, or consisting of about 10% w/w ibudilast, about 35% w/w lactose monohydrate, about 33.5% w/w microcrystalline cellulose, about 20% w/w hypromellose, about 0.5% w/w magnesium stearate, and about 1% w/w colloidal silicon dioxide. In some embodiments, the method comprises administering to the subject a pharmaceutical composition comprising, consisting essentially of, or consisting of about 5% w/w ibudilast, about 37% w/w lactose, about 38.5% w/w microcrystalline cellulose, about 18% w/w hypromellose, about 0.5% w/w magnesium stearate, and about 1% w/w colloidal silicon dioxide. In some embodiments, the method comprises administering to the subject a pharmaceutical composition comprising, consisting essentially of, or consisting of 10% w/w ibudilast, about 35% w/w lactose, about 33.5% w/w microcrystalline cellulose, about 20% w/w hypromellose, about 0.5% w/w magnesium stearate, and about 1% w/w colloidal silicon dioxide. In some embodiments, the lactose is lactose monohydrate.

Methods of Treatment

In another aspect, any one of the compositions described herein are used to treat any one or more of the diseases or disorders described herein. Accordingly, a method to treat one or more of the diseases or disorders described herein using a therapeutically effective amount of a composition described herein is another aspect of this disclosure.

In some embodiments, the disease or disorder is neurodegenerative disease, hereditary biochemical disorder, progressive neurodegenerative disease, or symptoms thereof. Exemplary neurodegenerative diseases/disorders include, but are not limited to, Alzheimer's disease, Senile dementia of the Alzheimer type, or Pick's disease (lobar atrophy), multiple sclerosis, neurodegenerative diseases that include syndromes combining progressive dementia with other prominent neurologic abnormalities, progressive neurodegenerative disease mainly afflicting adults and including progressive neurodegenerative forms of Huntington's disease, multiple system atrophy combining dementia with ataxia and/or manifestation of Parkinson's disease, progressive supranuclear palsy (Steele-Richardson-Olszewski), diffuse Lewy body disease, or corticodentatinigral degeneration. Additional subjects can be suffering from progressive neurodegenerative disease that mainly afflicts young adults and children and include Hallervorden-Spatz disease and progressive familial myoclonic epilepsy, progressive neurodegenerative disease that includes syndromes of gradually developing abnormalities of posture and movement, or disease that includes paralysis agitans (Parkinson's disease), striatonigral degeneration, progressive supranuclear palsy, torsion dystonia (torsion spasm; dystonia musculorum deformans), spasmodic torticollis and other restricted dyskinesias, Familial tremor, or Gilles de la Tourette syndrome, syndromes of progressive ataxia, cerebellar degenerations or spinocerebellar degenerations, cerebellar cortical degeneration or olivopontocerebellar atrophy (OPCA), spinocerebellar degenerations including spinocerebellar degenerations (Friedreich's ataxia and related disorders). Neurodegenerative diseases/disorders include, but are not limited to, central autonomic nervous system failure (Shy-Drager syndrome), syndromes of muscular weakness and wasting without sensory changes (motor neuron disease), amyotrophic lateral sclerosis (ALS), spinal muscular atrophy, infantile spinal muscular atrophy (Werdnig-Hoffmann), juvenile spinal muscular atrophy (Wohlfart-Kugelberg-Welander), or other forms of familial spinal muscular atrophy, primary lateral sclerosis or hereditary spastic paraplegia, syndromes combining muscular weakness and wasting with sensory changes (progressive neural muscular atrophy; chronic familial polyneuropathies), peroneal muscular atrophy (Charcot-Marie-Tooth), hypertrophic interstitial polyneuropathy (Deferine-Sottas), or miscellaneous forms of chronic progressive neuropathy, progressive neurodegenerative diseases that include syndromes of progressive visual loss. Neurodegenerative diseases/disorders include, but are not limited to, pigmentary degeneration of the retina (retinitis pigmentosa), or hereditary optic atrophy (Leber's disease), motor neuron disease and the progressive ataxias; glaucoma; retinal detachment; sporadic progressive neurodegenerative diseases, multifocal motor neuropathy with conduction block, motor neuropathy with paraproeinemia, motor-predominant peripheral neuropathies, olivopontocerebellar atrophy, Azorean (Machado-Joseph) disease, familial progressive neurodegenerative diseases such as familial amyotrophic lateral sclerosis, spinal muscular atrophies, familial spastic paraparesis, hereditary biochemical disorders, arthrogryposis multiplex congenital, or progressive juvenile bulbar palsy (Fazio-Londe). Examples of hereditary biochemical disorders are superoxide dismutase deficiency, hexosaminidase A and B deficiency, or androgen receptor mutation (Kennedy's syndrome). Progressive neurodegenerative diseases can include viral and prion diseases, such as HTL V-1 associated myelopathy, progressive multifocal leukoencephalopathy, Creutzfeldt-Jakob disease, Gerstmann-Straussler-Scheinker disease, kuru, fatal familial insomnia, or Alper's disease.

"Progressive neurodegenerative disease" means any neurodegenerative disease that is in the progressive state (that is, getting worse compared to a baseline level) or has such progressive characteristics. Thus, a progressive state is a worsening of symptoms over time and can be precipitous or gradual. Examples of progressive neurodegenerative diseases include Parkinson's disease, amyotrophic lateral sclerosis, Alzheimer's disease, and progressive forms of multiple sclerosis exclusive of relapse/remitting multiple sclerosis.

In some embodiments, the disease or disorder is an ophthalmic disease/disorder or injury associated with a neurodegenerative disease/disorder or a neuro-ophthalmologic disorder. In some embodiments, the ophthalmic disease/disorder or injury is retinal injury. In some embodiments, the ophthalmic disease/disorder or injury is macular injury. In some embodiments, the ophthalmic disease/disorder or injury is macular thinness. In some embodiments, the neurodegenerative disease/disorder is progressive multiple sclerosis. Exemplary neuro-ophthalmologic disorders include, but are not limited to, papilledema and idiopathic intracranial hypertension (IIH); anterior ischemic optic neuropathy (AION); optic neuritis; ocular motor cranial neuropathy; and Horner syndrome.

In some embodiments, the disease or disorder is alcoholism and depression and/or dysphoric mood. Examples include alcohol use disorder (AUD) that may be accompanied with depression or dysphoric mood. In some embodiments, the depression is mild depression, moderate depression, or severe depression. In some embodiments, the dysphoric mood is higher dysphoric mood, moderate dysphoric mood, or lower dysphoric mood.

In some embodiments, the disease or disorder is glioblastoma, recurrent glioblastoma or its associated symptoms. In some embodiments, the disease or disorder is glioblastoma. In some embodiments, the disease or disorder is recurrent glioblastoma.

For treating glioblastoma or recurrent glioblastoma, in some embodiments, the patient is a human patient. In some embodiments, the patient has extra copies of the epidermal growth factor receptor (EGFR) gene or expresses abnormally high levels of EGFR. In some embodiments, the abnormally high levels of EGRF refers to higher levels of EGRF in a cancer patient relative to lower levels of EGFR in cancer-free individuals. In some embodiments, the patient lacks heterozygosity in chromosome 10. In some embodiments, the patient displays chromosome 7 amplification. In some embodiments, the patient has a mutated gene selected from the group consisting of TP53, PDGFRA, IDH1, PTEN and NF1. In some embodiments, the patient expresses NEFL, GABRA1, SYT1 or SLC12A5.

In some embodiments, the disease or disorder is multiple sclerosis or progressive multiple sclerosis. There are four recognized types of multiple sclerosis: (1) Relapsing/Remitting Multiple Sclerosis (RR multiple sclerosis), (2) Secondary Progressive Multiple Sclerosis (SP multiple sclerosis), (3) Progressive Relapsing Multiple Sclerosis (PR multiple sclerosis), and (4) Primary Progressive Multiple Sclerosis (PP multiple sclerosis). RR multiple sclerosis is not considered to fall within the scope of the claims, but the other forms of multiple sclerosis, i.e., SP multiple sclerosis, PR multiple sclerosis and PP multiple sclerosis are considered to be one aspect of the present invention. In all types of progressive MS, there is a loss of function over time regardless of relapses.

"Relapsing/Remitting Multiple Sclerosis (RR multiple Sclerosis) is characterized by relapses (also known as exacerbations) during which time new symptoms can appear and old ones resurface or worsen. The relapses are followed by periods of remission, during which time the person fully or partially recovers from the deficits acquired during the relapse. Relapses can last for days, weeks or months and recovery can be slow and gradual or almost instantaneous. The vast majority of people presenting with Multiple Sclerosis are first diagnosed with relapsing/remitting. This is typically when they are in their twenties or thirties, though diagnoses much earlier or later are known. Around twice as many women as men present with this variety.

In "Secondary Progressive Multiple Sclerosis (SP multiple Sclerosis), a person who initially had relapsing-remitting multiple Sclerosis begins to develop a gradual deterioration in nerve function, with or without relapses. After a number of years many people who have had relapsing/remitting multiple Sclerosis will pass into a secondary progressive phase of the disease. This is characterized by a gradual worsening of the disease between relapses. In the early phases of Secondary Progressive MS, the person may still experience a few relapses but after a while, these merge into a general progression. People often do not return to their prior level of function after a relapse. People with Secondary Progressive MS may experience good and bad days or weeks, but, apart from some remission following relapsing episodes, have no real recovery. After 10 years, 50% of people with relapsing/remitting multiple sclerosis will have developed secondary progressive. By 25 to 30 years, that figure will have risen to 90%.

"Progressive Relapsing Multiple Sclerosis (PR multiple sclerosis) shows clear progression in the level of disability from the time symptoms first begin, but with episodes of clear relapses that may or may not be associated with some recovery following the acute episode. This form of multiple sclerosis follows a progressive course from onset, punctuated by relapses. There is significant recovery immediately following a relapse but between relapses, there is a gradual worsening of symptoms.

"Primary Progressive Multiple Sclerosis (PP multiple sclerosis) is characterized by a gradual progression of the disease from its onset with no remissions or relapses at all. There may be periods of a leveling off of disease activity and, as with secondary progressive, there may be good and bad days or weeks. PP multiple sclerosis differs from Relapsing/Remitting MS and Secondary Progressive MS in that onset is typically in the late thirties or early forties, men are as likely women to develop it and initial disease activity is in the spinal cord and not in the brain. Primary Progressive multiple sclerosis often migrates into the brain, but is less likely to damage brain areas than relapsing/remitting or secondary progressive—for example, people with Primary Progressive MS are less likely to develop cognitive problems.

In some embodiments, the progressive multiple sclerosis has progressed beyond relapse remitting multiple sclerosis. In some embodiments, the progressive multiple sclerosis is primary progressive multiple sclerosis. In some embodiments, the primary progressive multiple sclerosis is characterized by disease progression from onset, with occasional plateaus and temporary minor improvements allowed, but not distinct relapses. In some embodiments, the progressive multiple sclerosis is secondary progressive multiple sclerosis. In some embodiments, the secondary progressive multiple sclerosis is characterized as an initial relapsing-remitting course, followed by progression, with or without occasional relapses, minor remissions and plateaus.

In some embodiments, the disease or disorder is uveal melanoma.

In some embodiments, the disease or disorder is chemotherapy-induced muscle toxicity and/or chemotherapy-induced cardio-toxicity. In some embodiments, the disease or disorder is chemotherapy-induced neuropathy.

In another aspect, any one of the compositions described herein are used in a method of suppressing myeloid-derived suppressor cells (MDSCs) in a patient diagnosed with cancer or suffering therefrom, the method comprising administering to the patient a therapeutically effective amount of the composition described herein.

In another aspect, any one of the compositions described herein are used in a method of reducing immune suppression in a patient diagnosed with cancer or suffering therefrom, the method comprising administering to the patient a therapeutically effective amount of the composition described herein.

In another aspect, any one of the compositions described herein are used in a method of reducing regulatory T-cell count in a patient diagnosed with cancer or suffering therefrom, the method comprising administering to the patient a therapeutically effective amount of the composition described herein.

In another aspect, any one of the compositions described herein are used in a method of increasing CD4+ T-cell count in a patient diagnosed with cancer or suffering therefrom, the method comprising administering to the patient a therapeutically effective amount of the composition described herein.

In some embodiments, the cancer is a cancer of the circulatory system selected from angiosarcoma, fibrosarcoma, rhabdomyosarcoma, liposarcoma, myxoma, rhabdomyoma, fibroma, lipoma and teratoma, cancer of the mediastinum and pleura, or a vascular tumor; a cancer of the respiratory tract selected from cancer of the nasal cavity and middle ear, cancer of accessory sinuses, cancer of the larynx, cancer of the trachea, cancer of the bronchus and lung, small cell lung cancer (SCLC), non-small cell lung cancer (NSCLC), bronchogenic carcinoma, squamous cell carcinoma, undifferentiated small cell carcinoma, undifferentiated large cell carcinoma, adenocarcinoma, alveolar (bronchiolar) carcinoma, bronchial adenoma, sarcoma, lymphoma, chondromatous hamartoma or mesothelioma; a cancer of the gastrointestinal system selected from squamous cell carcinoma, adenocarcinoma, leiomyosarcoma, lymphoma, carcinoma, leiomyosarcoma, ductal adenocarcinoma, insulinoma, glucagonoma, gastrinoma, carcinoid tumors, vipoma, adenocarcinoma, carcinoid tumors, Karposi's sarcoma, leiomyoma, hemangioma, lipoma, neurofibroma, fibroma, adenocarcinoma, tubular adenoma, villous adenoma, hamartoma, or leiomyoma; a cancer of the genitourinary tract selected from adenocarcinoma, Wilm's tumor (nephroblastoma), lymphoma, leukemia, squamous cell carcinoma, transitional cell carcinoma, adenocarcinoma, adenocarcinoma, sarcoma of the prostate, seminoma, teratoma, embryonal carcinoma, teratocarcinoma, choriocarcinoma, interstitial cell carcinoma, fibroma, fibroadenoma, adenomatoid tumors, or lipoma; a cancer of the liver selected from hepatoma (hepatocellular carcinoma), cholangiocarcinoma, hepatoblastoma, angiosarcoma, hepatocellular adenoma, hemangioma, pheochromocytoma, insulinoma, vasoactive intestinal peptide tumor, islet cell tumor or glucagonoma; a cancer of the bone selected from osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma or giant cell tumors; a cancer of the nervous system selected from primary CNS lymphoma, osteoma, hemangioma, granuloma, xanthoma, osteitis deformans, meningioma, meningiosarcoma, gliomatosis, astrocytoma, medulloblastoma, glioma, ependymoma, germinoma (pinealoma), oligodendroglioma, schwannoma, retinoblastoma, congenital tumors, spinal cord neurofibroma, meningioma, glioma, or sarcoma; a cancer of the reproductive system selected from endometrial carcinoma, cervical carcinoma, pre-tumor cervical dysplasia, ovarian carcinoma, serous cystadenocarcinoma, mucinous cystadenocarcinoma, unclassified carcinoma, granulosa-thecal cell tumors, Sertoli-Leydig cell tumors, dysgerminoma, malignant teratoma, squamous cell carcinoma of the vulva, intraepithelial carcinoma of the vulva, adenocarcinoma of the vulva, fibrosarcoma of the vulva, melanoma of the vulva, vaginal clear cell carcinoma, vaginal squamous cell carcinoma, vaginal botryoid sarcoma (embryonal rhabdomyosarcoma), carcinoma of the fallopian tubes placental cancer, penile cancer, prostate cancer, or testicular cancer; a cancer of the hematologic system selected from myeloid, acute lymphoblastic leukemia, chronic lymphocytic leukemia, myeloproliferative diseases, multiple myeloma, myelodysplastic syndrome, Hodgkin's disease, or non-Hodgkin's lymphoma; a cancer of the oral cavity selected from lip cancer, tongue cancer, gum cancer, floor of mouth cancer, palate cancer, parotid gland cancer, salivary gland cancer, tonsil cancer, cancer of the oropharynx, cancer of the nasopharynx, pyriform sinus cancer, or cancer of the hypopharynx; a cancer of the skin selected from malignant melanoma, cutaneous melanoma, basal cell carcinoma, squamous cell carcinoma, Karposi's sarcoma, moles dysplastic nevi, lipoma, angioma, dermatofibroma or keloidal cancer; or a cancer selected from cancer of the adrenal glands, neuroblastoma, cancer of connective and soft tissue, cancer of the retroperitoneum and peritoneum, eye cancer, intraocular melanoma, uveal melanoma, cancer of adnexa, breast cancer, head or/and neck cancer, anal cancer, thyroid cancer, parathyroid cancer, cancer of the adrenal gland, cancer of the endocrine glands and related structures, secondary and unspecified malignant neoplasm of lymph nodes, secondary malignant neoplasm of respiratory and digestive systems or secondary malignant neoplasm of other sites. In some embodiments, the cancer is glioblastoma multiforme (GBM). In some embodiments, the cancer is not glioblastoma multiforme (GBM).

In another aspect, any one of the compositions described herein are used in a method of suppressing myeloid-derived suppressor cells (MDSCs) in a patient diagnosed with microorganism infection or suffering therefrom, the method comprising administering to the patient a therapeutically effective amount of the composition described herein.

In another aspect, any one of the compositions described herein are used in a method of reducing immune suppression in a patient diagnosed with microorganism infection or suffering therefrom, the method comprising administering to the patient a therapeutically effective amount of the composition described herein.

In another aspect, any one of the compositions described herein are used in a method of reducing regulatory T-cell count in a patient diagnosed with microorganism infection or suffering therefrom, the method comprising administering to the patient a therapeutically effective amount of the composition described herein.

In another aspect, any one of the compositions described herein are used in a method of increasing CD4+ T-cell count in a patient diagnosed with microorganism infection or suffering therefrom, the method comprising administering to the patient a therapeutically effective amount of the composition described herein.

In another aspect, any one of the compositions described herein are used in a method of suppressing myeloid-derived suppressor cells (MDSCs) in a patient diagnosed with sepsis or suffering therefrom, the method comprising administering to the patient a therapeutically effective amount of the composition described herein.

In another aspect, any one of the compositions described herein are used in a method of reducing immune suppression in a patient diagnosed with sepsis or suffering therefrom, the method comprising administering to the patient a therapeutically effective amount of the composition described herein.

In another aspect, any one of the compositions described herein are used in a method of reducing regulatory T-cell count in a patient diagnosed with sepsis or suffering therefrom, the method comprising administering to the patient a therapeutically effective amount of the composition described herein.

In another aspect, any one of the compositions described herein are used in a method of increasing CD4+ T-cell count in a patient diagnosed with sepsis or suffering therefrom, the method comprising administering to the patient a therapeutically effective amount of the composition described herein.

Methods of Administration

In another aspect, the present disclosure is directed to oral administration of ibudilast, or pharmaceutically acceptable salt thereof. In terms of patient compliance and ease of administration, such an approach may be preferred, since patients are often averse to taking multiple pills or dosage forms, often multiple times daily, over the duration of treatment. In some embodiments, the ibudilast is administered in a single daily dosage form. In some embodiments, the single daily dosage form is a tablet. In some embodiments, the single daily dosage form is a capsule.

Dosages

Therapeutic amounts can be empirically determined and will vary with the particular condition being treated, the subject, and the efficacy and toxicity of each of the active agents contained in the composition. The actual dose to be administered will vary depending upon the age, weight, and general condition of the subject as well as the severity of the condition being treated, the judgment of the health care professional, and particular combination being administered.

Therapeutically effective amounts can be determined by those skilled in the art, and will be adjusted to the requirements of each particular case. Generally, a therapeutically effective amount of ibudilast or pharmaceutically acceptable salt thereof will range from a total daily dosage of about.

In some embodiments, the therapeutically effective amount of ibudilast or pharmaceutically acceptable salt thereof is at least about 5 mg, at least about 10 mg, at least about 20 mg, at least about 25 mg, at least about 30 mg, at least about 35 mg, at least about 40 mg, at least about 45 mg, at least about 50 mg, at least about 55 mg, at least about 60 mg, at least about 65 mg, at least about 70 mg, at least about 75 mg, at least about 80 mg, at least about 85 mg, at least about 90 mg, at least about 95 mg, at least about 100 mg, at least about 110 mg, at least about 120 mg, at least about 130 mg, at least about 140 mg, at least about 150 mg, at least about 160 mg, at least about 170 mg, at least about 180 mg, at least about 190 mg, or at least about 200 mg. In some embodiments, the therapeutically effective amount of ibudilast or pharmaceutically acceptable salt thereof is at least about 50 mg.

In some embodiments, the therapeutically effective amount of ibudilast or pharmaceutically acceptable salt thereof is from about 5 mg to about 10 mg, 5 mg to about 20 mg, 5 mg to about 30 mg, 5 mg to about 40 mg, 5 mg to about 50 mg, 5 mg to about 60 mg, 5 mg to about 70 mg, 5 mg to about 80 mg, 5 mg to about 90 mg, 5 mg to about 100 mg, 5 mg to about 150 mg, 5 mg to about 200 mg, 10 mg to about 20 mg, 10 mg to about 30 mg, 10 mg to about 40 mg, 10 mg to about 50 mg, 10 mg to about 60 mg, 10 mg to about 70 mg, 10 mg to about 80 mg, 10 mg to about 90 mg, 10 mg to about 100 mg, 10 mg to about 150 mg, 10 mg to about 200 mg, 20 mg to about 30 mg, 20 mg to about 40 mg, 20 mg to about 50 mg, 20 mg to about 60 mg, 20 mg to about 70 mg, 20 mg to about 80 mg, 20 mg to about 90 mg, 20 mg to about 100 mg, 20 mg to about 250 mg, 20 mg to about 200 mg, 30 mg to about 40 mg, 30 mg to about 50 mg, 30 mg to about 60 mg, 30 mg to about 70 mg, 30 mg to about 80 mg, 30 mg to about 90 mg, 30 mg to about 100 mg, 30 mg to about 250 mg, 30 mg to about 200 mg, 40 mg to about 50 mg, 40 mg to about 60 mg, 40 mg to about 70 mg, 40 mg to about 80 mg, 40 mg to about 90 mg, 40 mg to about 100 mg, 40 mg to about 250 mg, 40 mg to about 200 mg, 50 mg to about 60 mg, 50 mg to about 70 mg, 50 mg to about 80 mg, 50 mg to about 90 mg, 50 mg to about 100 mg, 50 mg to about 250 mg, or 50 mg to about 200 mg. In some embodiments, the therapeutically effective amount of ibudilast or pharmaceutically acceptable salt thereof is from about 10 mg to about 100 mg.

In some embodiments, the therapeutically effective amount of ibudilast or pharmaceutically acceptable salt thereof is about 5 mg, about 10 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, or about 200 mg. In some embodiments, the therapeutically effective amount of ibudilast or pharmaceutically acceptable salt thereof is about 50 mg.

In some embodiments, the therapeutically effective amount of ibudilast or pharmaceutically acceptable salt thereof is at least about 5 mg/day, at least about 10 mg/day, at least about 20 mg/day, at least about 25 mg/day, at least about 30 mg/day, at least about 35 mg/day, at least about 40 mg/day, at least about 45 mg/day, at least about 50 mg/day, at least about 55 mg/day, at least about 60 mg/day, at least about 65 mg/day, at least about 70 mg/day, at least about 75 mg/day, at least about 80 mg/day, at least about 85 mg/day, at least about 90 mg/day, at least about 95 mg/day, at least about 100 mg/day, at least about 110 mg/day, at least about 120 mg/day, at least about 130 mg/day, at least about 140 mg/day, at least about 150 mg/day, at least about 160 mg/day, at least about 170 mg/day, at least about 180 mg/day, at least about 190 mg/day, or at least about 200 mg/day. In some embodiments, the therapeutically effective amount of ibudilast or pharmaceutically acceptable salt thereof is at least about 50 mg/day.

In some embodiments, the therapeutically effective amount of ibudilast or pharmaceutically acceptable salt thereof is from about 5 mg/day to about 10 mg/day, 5 mg/day to about 20 mg/day, 5 mg/day to about 30 mg/day, 5 mg/day to about 40 mg/day, 5 mg/day to about 50 mg/day, 5 mg/day to about 60 mg/day, 5 mg/day to about 70 mg/day, 5 mg/day to about 80 mg/day, 5 mg/day to about 90 mg/day, 5 mg/day to about 100 mg/day, 5 mg/day to about 150 mg/day, 5 mg/day to about 200 mg/day, 10 mg/day to about 20 mg/day, 10 mg/day to about 30 mg/day, 10 mg/day to about 40 mg/day, 10 mg/day to about 50 mg/day, 10 mg/day to about 60 mg/day, 10 mg/day to about 70 mg/day, 10 mg/day to about 80 mg/day, 10 mg/day to about 90 mg/day, 10 mg/day to about 100 mg/day, 10 mg/day to about 150 mg/day, 10 mg/day to about 200 mg/day, 20 mg/day to about 30 mg/day, 20 mg/day to about 40 mg/day, 20 mg/day to about 50 mg/day, 20 mg/day to about 60 mg/day, 20 mg/day to about 70 mg/day, 20 mg/day to about 80 mg/day, 20 mg/day to about 90 mg/day, 20 mg/day to about 100 mg/day, 20 mg/day to about 250 mg/day, 20 mg/day to about 200 mg/day, 30 mg/day to about 40 mg/day, 30 mg/day to about 50 mg/day, 30 mg/day to about 60 mg/day, 30 mg/day to about 70 mg/day, 30 mg/day to about 80 mg/day, 30 mg/day to about 90 mg/day, 30 mg/day to about 100 mg/day, 30 mg/day to about 250 mg/day, 30 mg/day to about 200 mg/day, 40 mg/day to about 50 mg/day, 40 mg/day to about 60 mg/day, 40 mg/day to about 70 mg/day, 40 mg/day to about 80 mg/day, 40 mg/day to about 90 mg/day, 40 mg/day to about 100 mg/day, 40 mg/day to about 250 mg/day, 40 mg/day to about 200 mg/day, 50 mg/day to about 60 mg/day, 50 mg/day to about 70 mg/day, 50 mg/day to about 80 mg/day, 50 mg/day to about 90 mg/day, 50 mg/day to about 100 mg/day, 50 mg/day to about 250 mg/day, or 50 mg/day to about 200 mg/day. In some embodiments, the therapeutically effective amount of ibudilast or pharmaceutically acceptable salt thereof is from about 10 mg/day to about 100 mg/day.

In some embodiments, the therapeutically effective amount of ibudilast or pharmaceutically acceptable salt thereof is about 5 mg/day, about 10 mg/day, about 20 mg/day, about 25 mg/day, about 30 mg/day, about 35 mg/day, about 40 mg/day, about 45 mg/day, about 50 mg/day, about 55 mg/day, about 60 mg/day, about 65 mg/day, about 70 mg/day, about 75 mg/day, about 80 mg/day, about 85 mg/day, about 90 mg/day, about 95 mg/day, about 100 mg/day, about 110 mg/day, about 120 mg/day, about 130 mg/day, about 140 mg/day, about 150 mg/day, about 160 mg/day, about 170 mg/day, about 180 mg/day, about 190 mg/day, or about 200 mg/day. In some embodiments, the therapeutically effective amount of ibudilast or pharmaceutically acceptable salt thereof is about 50 mg/day.

Depending upon the dosage amount and precise condition to be treated, administration can be one, two, three, or four times daily for a time course of one day to several days, weeks, months, and even years, and may even be for the life of the patient. Illustrative dosing regimens will last a period of at least about a week, from about 1-4 weeks, from about 1-8 weeks, from 1-12 weeks, from 1-16 weeks, from 1-20 weeks, from 1-24 weeks, from 1-36 weeks, from 1-48 weeks, from 1-52 weeks, from 1-60 weeks, from 1-72 weeks, from 1-84 weeks, from 1-96 weeks, from 1 week to 1 year, from 1 week to 2 years, from 1 week to 3 years, from 1 week to 4 years, from 1 week to 5 years, or longer. In some embodiments, the dosing regimen is for a period of at least about 12, 24, 36, 48, 60, 72, 84, or 96 weeks. In some embodiments, the dosing regimen is for a period of about 12, 24, 36, 48, 60, 72, 84, or 96 weeks. In some embodiments, the dosing regimen is for a period of at least about 1 year, 2 years, 3 years, 4 years, or 5 years. In some embodiments, the dosing regimen is for a period of about 1 year, 2 years, 3 years, 4 years, or 5 years.

Practically speaking, a unit dose of any given composition of the disclosure or active agent can be administered in a variety of dosing schedules, depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, every other day, three times weekly, twice weekly, once weekly, twice monthly, once monthly, and so forth.

Excipients/Carriers

The compositions of the disclosure may further comprise one or more additional pharmaceutically acceptable excipients or carriers. Exemplary excipients include, without limitation, polyethylene glycol (PEG), PEG 400, (2-hydroxypropyl)-β-cyclodextrin, hydrogenated castor oil (HCO), cremophors, carbohydrates, starches (e.g., corn starch), inorganic salts, antimicrobial agents, antioxidants, binders/fillers, surfactants, lubricants (e.g., calcium stearate), glidants such as talc, disintegrants, diluents, buffers, acids, bases, film coats, combinations thereof, and the like. In some embodiments, the composition is devoid of hydrogenated castor oil. In some embodiments, the composition is devoid of hydroxypropyl methylcellulose-phthalate. In some embodiments, the composition is devoid of hydrogenated castor oil and hydroxypropyl methylcellulose-phthalate.

A composition of the disclosure may further include one or more carbohydrates such as a sugar, a derivatized sugar such as an alditol, aldonic acid, an esterified sugar, and/or a sugar polymer. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

Also suitable for use in the compositions of the disclosure are potato and corn-based starches such as sodium starch glycolate and directly compressible modified starch.

Further representative excipients include inorganic salt or buffers such as citric acid, sodium chloride, potassium chloride, sodium sulfate, potassium nitrate, sodium phosphate monobasic, sodium phosphate dibasic, and combinations thereof.

A composition of the disclosure may also optionally contain one or more antioxidants. Antioxidants are used to prevent oxidation, thereby preventing the deterioration of the drug(s) or other components of the preparation. Suitable antioxidants for use in the present disclosure include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

Additional exemplary excipients include surfactants such as polysorbates, e.g., "Tween 20" and "Tween 80," and pluronics such as F68 and F88 (both of which are available from BASF, Mount Olive, N.J.), sorbitan esters, lipids (e.g., phospholipids such as lecithin and other phosphatidylcholines, and phosphatidylethanolamines), fatty acids and fatty esters, steroids such as cholesterol, and chelating agents, such as EDTA, zinc and other such suitable cations.

Further, a composition of the disclosure may optionally include one or more acids or bases. Non-limiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Non-limiting examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumarate, and combinations thereof.

The amount of any individual excipient in the composition will vary depending on the role of the excipient, the dosage requirements of the active agent components, and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, an additional excipient will be present in the composition in an amount of about 0.1% to about 25% by weight of the composition. In general, the amount of excipient present in an ibudilast composition of the disclosure is selected from the following: at least about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% by weight of the composition (% w/w), including increments therein.

These foregoing pharmaceutical excipients along with other excipients are described in "Remington: The Science & Practice of Pharmacy", 19th ed., Williams & Williams, (1995), the "Physician's Desk Reference", 52.sup.nd ed., Medical Economics, Montvale, N.J. (1998), and Kibbe, A. H., Handbook of Pharmaceutical Excipients, 3.sup.rd Edition, American Pharmaceutical Association, Washington, D.C., 2000.

Other Actives

A formulation (or kit) in accordance with the disclosure may contain, in addition to ibudilast or a pharmaceutically acceptable salt thereof, one or more additional active agents. In some embodiments, the one or more other therapeutic agent is one that possesses a mechanism of action different from that of ibudilast. Such active ingredients can be found listed in the FDA's Orange Book, Goodman & Gilman The Pharmacological Basis of Therapeutics, J. Griffith Hardman, L. L. Limbird, A. Gilman, 11th Ed., 2005, The Merck Manual, 18th edition, 2007, and The Merck Manual of Medical Information 2003.

Delivery Forms

The compositions described herein encompass all types of oral formulations. Oral dosage forms include tablets, lozenges, capsules, syrups, oral suspensions, emulsions, granules, microbeads, and pellets. In some embodiments, the oral dosage form is a tablet, capsule, granule, or microbead dosage form. In some embodiments, the oral dosage form is a tablet. In some embodiments, the tablet is an extended release tablet. In some embodiments, the oral dosage form is a capsule. In some embodiments, the capsule is an extended release capsule. In some embodiments, the oral dosage form is in a liquid dosage form. In some embodiments, the oral dosage form is an extended release formulation.

Alternative formulations include powders or lyophilates that can be reconstituted as well as liquids. With respect to liquid pharmaceutical compositions, solutions and suspensions are envisioned.

Tablets can be made by compression or molding, optionally with one or more accessory ingredients or additives. Compressed tablets are prepared, for example, by compressing in a suitable tabletting machine, the active ingredients in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) and/or surface-active or dispersing agent.

Molded tablets are made, for example, by molding in a suitable tabletting machine, a mixture of powdered compounds moistened with an inert liquid diluent. The tablets may optionally be coated or scored, and may be formulated so as to provide slow or controlled release of the active ingredients, using, for example, hydroxypropylmethyl cellulose in varying proportions to provide the desired release profile. Tablets may optionally be provided with a coating, such as a thin film, sugar coating, or an enteric coating to provide release in parts of the gut other than the stomach. Processes, equipment, and toll manufacturers for tablet and capsule making are well-known in the art.

A formulation of the disclosure may also be an extended release formulation, such that each of the drug components is released or absorbed slowly over time, when compared to a non-sustained release formulation. In some embodiments, the compositions are formulated in order to improve stability and extend the half-life of ibudilast or the pharmaceutically acceptable salt thereof. For example, ibudilast or the pharmaceutically acceptable salt thereof is delivered in a controlled or extended-release formulation. Controlled or extended-release formulations are prepared by incorporating ibudilast or the pharmaceutically acceptable salt thereof into a carrier or vehicle such as liposomes, nonresorbable impermeable polymers such as ethylenevinyl acetate copolymers and HYTREL® copolymers, swellable polymers such as hydrogels, or resorbable polymers such as collagen and certain polyacids or polyesters such as those used to make resorbable sutures. Additionally, ibudilast or the pharmaceutically acceptable salt thereof can be encapsulated, adsorbed to, or associated with, particulate carriers. Examples of particulate carriers include those derived from polymethyl methacrylate polymers, as well as microparticles derived from poly(lactides) and poly(lactide-co-glycolides), known as PLG. See, e.g., Jeffery et al., Pharm. Res. (1993) 10:362-368; and McGee et al., J. Microencap. (1996).

Extended release polymers suitable for this purpose are known in the art and include hydrophobic polymers such as cellulose ethers. Non-limiting examples of suitable cellulose ethers include ethyl cellulose, cellulose acetate and the like; polyvinyl esters such as polyvinyl acetate, polyacrylic acid esters, methacrylic and acrylate polymers (pH-independent types); high molecular weight polyvinyl alcohols and waxes such as fatty acids and glycerides, methacrylic acid ester neutral polymers, polyvinyl alcohol-maleic anhydride copolymers and the like; ethylacrylate-methylmethacrylate copolymers; aminoalkyl methacrylate copolymers; and mixtures thereof.

Sustained release formulations may employ pro-drug forms of the active agent, delayed-release drug delivery systems such as liposomes or polymer matrices, hydrogels, or covalent attachment of a polymer such as polyethylene glycol to the active agent.

In addition to the ingredients particularly mentioned above, the formulations of the disclosure may optionally include other agents conventional in the pharmaceutical arts and particular type of formulation being employed, for example, for oral administration forms, the composition for oral administration may also include additional agents as sweeteners, thickeners or flavoring agents.

Kits

Also provided herein is a kit containing any one of the compositions of the disclosure, accompanied by instructions for use.

For example, the kit comprises ibudilast, or pharmaceutically acceptable salt thereof, along with instructions for use. The ibudilast, or pharmaceutically acceptable salt thereof, and may be packaged in any manner suitable for administration, so long as the packaging, when considered along with the instructions for administration, clearly indicates the manner in which the drug components is to be administered.

For example, in an illustrative kit comprising ibudilast, or pharmaceutically acceptable salt thereof, the kit may be organized by any appropriate time period, such as by day. As an example, for Day 1, a representative kit may comprise unit dosages of each of ibudilast, or pharmaceutically acceptable salt thereof. If each of the drugs is to be administered twice daily, then the kit may contain, corresponding to Day 1, two rows of unit dosage forms of each of ibudilast, or pharmaceutically acceptable salt thereof, along with instructions for the timing of administration. Alternatively, if ibudilast, or pharmaceutically acceptable salt thereof, differ in the timing or quantity of administration, then such would be reflected in the packaging and instructions. Various embodiments according to the above may be readily envisioned, and would of course depend upon the particular combination of drugs, in addition to ibudilast, or pharmaceutically acceptable salt thereof, employed for treatment, their corresponding dosage forms, recommended dosages, intended patient population, and the like. The packaging may be in any form commonly employed for the packaging of pharmaceuticals, and may utilize any of a number of features such as different colors, wrapping, tamper-resistant packaging, blister packs, desiccants, and the like.

It is to be understood that while the disclosure has been described in conjunction with preferred specific embodiments, the foregoing description as well as the examples that follow are intended to illustrate and not limit the scope of the disclosure. Other aspects, advantages and modifications within the scope of the disclosure will be apparent to those skilled in the art to which the disclosure pertains.

All references mentioned in this application, including any patents, published patent applications, books, handbooks, journal publications, or the FDA Orange Book are hereby incorporated by reference herein, in their entirety.

The following examples are given for the purpose of illustrating various embodiments of the disclosure and are not meant to limit the present disclosure in any fashion. One skilled in the art will appreciate readily that the present disclosure is well adapted to carry out the objects and obtain the ends and advantages mentioned, as well as those objects, ends and advantages inherent herein. The present examples, along with the methods described herein are presently representative of embodiments and are exemplary, and are not intended as limitations on the scope of the disclosure. Changes therein and other uses which are encompassed within the spirit of the disclosure as defined by the scope of the claims will occur to those skilled in the art.

EXAMPLES

Example 1. Ibudilast Composition I

TABLE 1

| Ingredient | % w/w |
| --- | --- |
| ibudilast | 5.0 |
| hypromellose (METHOCEL ™ K4M) | 18.0 |
| lactose (FAST FLO ®) | 37.0 |
| microcrystalline cellulose (AVICEL ® PH 101) | 38.5 |
| magnesium stearate | 0.5 |
| colloidal silicon dioxide | 1.0 |
| TOTAL | 100.0 |

Example 2. Ibudilast Tablet I-A

Using the formulation from Example 1, a 20 mg-dose tablet was prepared:

TABLE 2

| Ingredient | % w/w | mg/tablet |
| --- | --- | --- |
| ibudilast | 5.0 | 20.0 |
| hypromellose (METHOCEL ™ K4M) | 18.0 | 72.0 |
| lactose (FAST FLO ®) | 37.0 | 148.0 |
| microcrystalline cellulose (AVICEL ® PH 101) | 38.5 | 154.0 |
| magnesium stearate | 0.5 | 2.0 |
| colloidal silicon dioxide | 1.0 | 4.0 |
| TOTAL | 100.0 | 400.0 |

Example 3. Ibudilast Composition II

TABLE 3

| Ingredient | % w/w |
| --- | --- |
| ibudilast | 10.0 |
| hypromellose (METHOCEL ™ K4M) | 20.0 |
| lactose (FAST FLO ®) | 35.0 |
| microcrystalline cellulose (AVICEL ® PH 101) | 33.5 |
| magnesium stearate | 0.5 |
| colloidal silicon dioxide | 1.0 |
| TOTAL | 100.0 |

Example 4. Ibudilast Tablet II-A

Using the formulation from Example 3, a 30 mg-dose tablet was prepared:

TABLE 4

| Ingredient | % w/w | mg/tablet |
| --- | --- | --- |
| ibudilast | 10.0 | 30.0 |
| hypromellose (METHOCEL ™ K4M) | 20.0 | 60.0 |
| lactose (FAST FLO ®) | 35.0 | 105.0 |
| microcrystalline cellulose (AVICEL ® PH 101) | 33.5 | 100.5 |
| magnesium stearate | 0.5 | 1.5 |
| colloidal silicon dioxide | 1.0 | 3.0 |
| TOTAL | 100.0 | 300.0 |

Example 5. Ibudilast Tablet II-B

Using the formulation from Example 3, a 60 mg-dose tablet was prepared:

TABLE 5

| Ingredient | % w/w | mg/tablet |
| --- | --- | --- |
| ibudilast | 10.0 | 60.0 |
| hypromellose (METHOCEL ™ K4M) | 20.0 | 120.0 |
| lactose (FAST FLO ®) | 35.0 | 210.0 |
| microcrystalline cellulose (AVICEL ® PH 101) | 33.5 | 201.0 |

TABLE 5-continued

| Ingredient | % w/w | mg/tablet |
|---|---|---|
| magnesium stearate | 0.5 | 3.0 |
| colloidal silicon dioxide | 1.0 | 6.0 |
| TOTAL | 100.0 | 600.0 |

Example 6. Ibudilast Composition III

TABLE 6

| Ingredient | % w/w |
|---|---|
| ibudilast | 10.0 |
| lactose monohydrate (FAST FLO ® 316) | 35.0 |
| microcrystalline cellulose (AVICEL ® PH 101) | 33.5 |
| hypromellose (METHOCEL ™ K4M) | 20.0 |
| magnesium stearate | 0.5 |
| colloidal silicon dioxide (AEROSIL ® 200) | 1.0 |
| TOTAL | 100.0 |

This formulation may be used to prepare forms of varying dosages of ibudilast.

Example 7. Ibudilast Tablet III-A

Using the formulation from Example 6, a 50 mg-dose tablet was prepared:

TABLE 7

| Ingredient | % w/w | mg/tablet |
|---|---|---|
| core tablet | | |
| ibudilast | 10.0 | 50.0 |
| lactose monohydrate (FAST FLO ® 316) | 35.0 | 175.0 |
| microcrystalline cellulose (AVICEL ® PH 101) | 33.5 | 167.5 |
| hypromellose (METHOCEL ™ K4M) | 20.0 | 100.0 |
| magnesium stearate | 0.5 | 2.5 |
| colloidal silicon dioxide (AEROSIL ® 200) | 1.0 | 5.0 |
| Total of core tablet | 100.0 | 500.0 |
| film coating material | | |
| OPADRY ® II Yellow 30G520002 | 3% w/w of core tablet | 15.0 |
| purified water* | N/A | q.s. |
| Total of coated tablet | 100.0 | 515.0 |

*coating dispersion to be prepared; 15% w/w solid content for the tablet

Lower dose tablets (e.g., 20 mg, 25 mg, 30 mg, 35 mg, 40 mg, or 45 mg) may be prepared similarly, using the formulation of Example 6.

Example 8. Ibudilast Tablet III-B

Using the formulation from Example 6, a 50 mg-dose tablet was prepared:

TABLE 8

| Ingredient | % w/w | mg/tablet |
|---|---|---|
| core tablet | | |
| ibudilast | 10.0 | 50.0 |
| lactose monohydrate (FAST FLO ® 316) | 35.0 | 175.0 |
| microcrystalline cellulose (AVICEL ® PH 101) | 33.5 | 167.5 |
| hypromellose (METHOCEL ™ K4M) | 20.0 | 100.0 |
| magnesium stearate | 0.5 | 2.5 |
| colloidal silicon dioxide (AEROSIL ® 200) | 1.0 | 5.0 |
| Total of core tablet | 100.0 | 500.0 |
| enteric coating material | | |
| methacrylic acid and ethyl acrylate copolymer dispersion (EUDRAGIT ® L30D55) | 3% w/w of core tablet | 33.33 (10.00)** |
| triethyl citrate | | 1.00 |
| talc | | 4.00 |
| purified water* | N/A | q.s. |
| Total of coated tablet | 100.0 | 515.00 |

*coating dispersion to be prepared; 15% w/w solid content for the tablet
**EUDRAGIT ® L30D55 is a 30% w/w solid dispersion Lower dose tablets (e.g., 20 mg, 25 mg, 30 mg, 35 mg, 40 mg, or 45 mg) may be prepared similarly, using the formulation of Example 6.

Example 9. Ibudilast Capsule III-C

Varying ibudilast dosages in capsule form (e.g., 20 mg, 25 mg, 30 mg, 35 mg, 40 mg, 45 mg, or 50 mg) are prepared by filling an empty capsule with the formulation from Example 6, adjusting the fill weight according to desired dosage.

Example 10. Dissolution Testing

Ibudilast tablet II-B (Example 4), tablet III-A (Example 7), and tablet III-B (Example 8) were assessed for their respective dissolution profiles at 4-, 7-, 12-, 15-, 18-, and 24-hour time points when tested in USP Apparatus Type II at (a) 50 rpm in 900 mL of simulated gastric fluid medium at 37° C. for 2 hours, followed by (b) 50 rpm in 900 mL of phosphate buffer with 0.3% w/w sodium lauryl sulfate at a pH of 6.8 at 37° C. for another 2-22 hours. Data for percent drug release at each time point is shown in Table 9.

TABLE 9

| Time Point (hour) | Tablet II-B (60 mg dose) | Tablet III-A (50 mg dose) | Tablet III-B (50 mg dose) | Control* (10 mg dose) |
|---|---|---|---|---|
| 2 | 13 | 17 | 0 | 10 |
| 4 | 30 | 36 | 15 | 56 |
| 7 | 48 | 48 | 33 | 79 |
| 12 | 71 | 66 | 59 | 91 |
| 15 | 82 | 75 | 69 | 96 |
| 18 | 90 | 83 | 79 | 97 |
| 24 | 97 | 91 | 89 | 101 |

*commercially available 10-mg dose ibudilast immediate release (IR) capsule from PINATOS ®

Example 11. Phase I Pharmacokinetics Study of Extended Release, High Dose Ibudilast Tablet in Healthy Volunteers (Part 1)

Because of the high daily dose levels (60-100 mg/day) required to achieve neuroprotective effect in target indications (e.g., progressive MS, drug addiction, amyotrophic lateral sclerosis), patients take a large number of capsules (6-10 capsules/day). This study investigated the pharmacokinetics, safety, and tolerability of two extended release (ER) formulations (Tablet III-A and Tablet III-B) compared with a commercially available 10-mg ibudilast immediate release (IR) capsule (PINATOS®).

Plasma concentration-time data for ibudilast were received from 12 subjects who participated in this randomized, three-way crossover study. Each subject received the following three treatments:
Two doses of 50 mg of ibudilast administered 12 hours apart (IR capsule)
A 100 mg single dose of Tablet III-A (administered as 2×50 mg tablets)
A 100 mg single dose of Tablet III-B (administered as 2×50 mg tablets)

Each treatment was separated by a 14-day washout period. Samples were collected up to 168 hours after dosing in each study period.

Plasma concentrations were subjected to noncompartmental analysis. Nominal sampling times were used in this analysis. Plasma samples below the limit of quantitation (BLQ) before the first quantifiable concentration were replaced with "0" for pharmacokinetic parameter calculations, while other BLQ samples were reported as missing. The following parameters were calculated:

| | |
|---|---|
| $t_{1/2}$ | Terminal half-life calculated as $\ln(2)/\lambda_z$, where $\lambda_z$ is the terminal rate constant calculated using the least-squares log-linear regression of the terminal phase. |
| $t_{max}$ | Time to reach maximum concentration. |
| $C_{max}$ | Maximum concentration, obtained by inspection. |
| $AUC_t$ | Area under the plasma concentration vs time curve from time zero to time t (time of last quantifiable plasma concentration), calculated by the linear trapezoidal rule. |
| $AUC_{0-\infty}$ | Area under the plasma concentration vs time curve from time zero to infinity, calculated as $AUCt + C_{last}/\lambda_z$, where $C_{last}$ is the last quantifiable concentration. |
| F | Relative bioavailability calculated as the quotient of AUC of the ER formulation and the IR formulation |

The pre-dose plasma concentrations in Periods 2 and 3 were measurable in several subjects, suggesting some carryover from the previous dose. These pre-dose concentrations were low relative to $C_{max}$ and therefore were replaced with 0 in the analysis. However, since these concentrations were also the 168-hour samples in Periods 1 and 2, they were added as originally reported for that time point. Steady-state MN-166 concentrations were estimated by nonparametric superposition of both the individual and average single dose concentration-time data, and those estimated steady-state concentrations were subjected to noncompartmental analysis as well.

The average plasma concentration time profiles were comparable across the three formulations. The plasma concentrations were highly variable both within and across subjects.

The average $t_{max}$ was 4.17 and 9.67 hours for formulations Tablet III-A and Tablet III-B, respectively, suggesting a faster absorption rate from the Tablet III-A formulation. As such, the average $C_{max}$ was about 20% higher for Tablet III-A (57.1 ng/mL) relative to Tablet III-B (45.1 ng/mL). Of note, the absorption lag time observed with the Tablet III-B formulation may have contributed to the delayed $t_{max}$. The extent of absorption, measured by AUC, after single dose administration was also slightly higher for Tablet III-A (1840 ng*h/mL) compared to the Tablet III-B formulation (1640 ng*h/mL).

Compared to the IR formulation, the $C_{max}$ for the Tablet III-A and the Tablet III-B formulations were about 30% and 10% higher, respectively, despite the 2-fold increase in the morning dose. This suggests that both Tablet III-A and Tablet III-B exhibited extended-release properties. Average AUC for the IR formulation (1790 ng*h/mL) was comparable to the Tablet III-A formulation and was slightly higher (9%) on average compared to the Tablet III-B formulation.

The relative bioavailability, calculated as the individual AUC ratio of the ER formulations to the IR formulation, averaged 104% and 94% for the Tablet III-A and the Tablet III-B formulations, respectively, suggesting comparable relative bioavailability for all three formulations. Of note, relative bioavailability ranged from 62 to 148% for Tablet III-A and from 47 to 156% for Tablet III-B, attesting to the high variability.

The terminal half-life was comparable for all three formulations, averaging between 52 and 58 hours.

Considering the high variability, both the average and the individual plasma concentration time profiles were extrapolated to steady state. Overall, the 24-hour steady-state levels were comparable across the three formulations. The average steady state extrapolated PK parameters are also comparable for the three formulations. Lastly, for the most part, the exposures were consistent within each subject across the formulations.

Example 12. Phase I Pharmacokinetics Study of Extended Release, High Dose Ibudilast Tablet in Healthy Volunteers (Part 2)

The 12 subjects from Example 11 further participated in a subsequent study. Subjects were randomized to receive (1) an ER formulation (Tablet III-A), or (2) the IR formulation (a commercially available 10-mg ibudilast immediate release (IR) capsule (PINATOS®) administered in the following fashion:
Dose titration phase (Days 1-3): Once-a-day doses of 50 mg of Tablet III-A (1 tablet) or 50 mg IR (five 10 mg capsules) for 3 days.
Multiple-dose phase (Days 4 to 14): Once-a-day doses of 100 mg of Tablet III-A (2 tablets) or twice-daily doses of 50 mg IR (5 capsules every 12 hours) for 11 days. On Day 14, only the morning dose was administered for the IR capsules.

Preliminary plasma concentration data were received and subjected to noncompartmental analysis. Parameters as described in Example 11 were calculated.

Overall preliminary conclusions:
For both formulations, average $t_{max}$ was reached within 3 hours after dosing. By 12-hours, the average plasma concentrations were only slightly higher for the ER formulation.
Higher variability was observed after the administration of the ER formulation with two subjects experiencing relatively high concentrations.
The steady state $C_{max}$ was on average comparable for the IR and the ER formulations.
The steady state $C_{min}$ and $AUC_{0-24}$ were lower for the ER formulation compared to the IR formulation.
The single dose data adequately predicted the steady state parameters for the IR formulation and less so for the ER formulation.
Final results are shown in Table 10.

TABLE 10

| Treatment | $t_{1/2}$ (h) | $t_{max}$ (h) | $C_{max}$ ng/mL | $AUC_{0-t}$ (h*ng/mL) | $AUC_{0-\infty}$ (h*ng/mL) | F (%) |
|---|---|---|---|---|---|---|
| IR Fasted | 55.2 ± 21.3 | 4 (2, 6) | 76.7 ± 14.6 | 1720 ± 575 | 1990 ± 744 | NA |
| ER Fasted | 70.2 ± 53.2 | 2 (2, 12) | 66.1 ± 19.1 | 1600 ± 457 | 1910 ± 606 | 99.0 ± 25.0 |
| ER Fed | 57.7 ± 23.1 | 6 (4, 24) | 119 ± 60.6 | 1890 ± 526 | 2160 ± 594 | 116 ± 22.9 |

Example 13. Phase I Pharmacokinetics Study of Extended Release, High Dose Ibudilast Tablet in Healthy Volunteers—Food Effect The objective of this study was (a) to examine the single dose pharmacokinetics (PK) and relative bioavailability of an extended-release (ER) tablet formulation of ibudilast (50-mg) compared to an immediate-release (IR) capsule formulation of ibudilast (five 10-mg capsules) in healthy volunteers in the fasted state; and (b) to examine the effect of food on the single-dose PK of an ER ibudilast 50-mg tablet formulation.

Tablet III-A and a commercially available 10-mg ibudilast immediate release (IR) capsule from PINATOS® were examined in this study.

Subjects received the following three treatments in a crossover fashion, administered one week apart:
  ER: Single dose (50 mg) of ER tablet administered without food (fasted state).
  ER: Single dose (50 mg) of ER tablet administered after a high calorie breakfast (fed state).
  IR: Single dose (50 mg) of the IR Formulation (five 10 mg IR capsules; PINATOS®) administered without food (fasted state).

Blood samples (approximately 2 mL per sample) were collected at pre-dose, 0.5, 1, 2, 4, 6, 8, 10, 12, 24, 32, 48, 72, 96, and 168 hours (last treatment of each sequence only) after dosing in each treatment.

Subjects followed a standard meal schedule with the exception of the morning of dosing day (Day 1, Day 8, and Day 15). After a snack on the evening of admission, subjects fasted overnight (10 hours). On the morning of dosing day, fasting continued until 4 hours after each study drug treatment in the fasted treatments. In the fed treatment, a high-fat (approximately 50 percent of total caloric content of the meal) and high-calorie (approximately 800 to 1000 calories) test meal was administered 30 minutes before dosing. This test meal derived approximately 150, 250, and 500-600 calories from protein, carbohydrate, and fat, respectively. Subjects ate this meal in 30 minutes or less. Standardized meals resumed 4 hours after dosing in all subjects and continued until they left the clinic 32 hours after dosing.

Preliminary plasma concentration data was received and subjected to noncompartmental analysis. Parameters as described in Example 11 were calculated. Results are shown in Table 10.

Para. A. A pharmaceutical composition comprising ibudilast and at least one pharmaceutically acceptable excipient, wherein said pharmaceutical composition is in the form of a tablet or a capsule, and wherein said tablet or said capsule has a dissolution profile wherein at least about 12% of said ibudilast has been released from said tablet or said capsule at about 2 hours when tested in USP Apparatus Type II at 50 rpm in 900 mL of simulated gastric fluid medium at 37° C.

Para. B. The pharmaceutical composition of Para. A, wherein the tablet has a coating comprising polyvinyl alcohol, plasticizer, and pigment.

Para. C. The pharmaceutical composition of Para. A or Para. B, wherein the at least one pharmaceutically acceptable excipient comprises microcrystalline cellulose, lactose, or hypromellose, or any combination of two or more thereof.

Para. D. The pharmaceutical composition of any one of Paras. A-C, wherein said tablet or said capsule has a dissolution profile wherein at least about 25% of said ibudilast has been released from said tablet or said capsule at about 4 hours when tested in USP Apparatus Type II at (a) 50 rpm in 900 mL of simulated gastric fluid medium at 37° C. for 2 hours, followed by (b) 50 rpm in 900 mL of phosphate buffer with 0.3% w/w sodium lauryl sulfate at a pH of 6.8 at 37° C. for another 2 hours.

Para. E. The pharmaceutical composition of any one of Paras. A-D, wherein said tablet or said capsule has a dissolution profile wherein at least about 60% of said ibudilast has been released from said tablet or said capsule at about 12 hours when tested in USP Apparatus Type II at (a) 50 rpm in 900 mL of simulated gastric fluid medium at 37° C. for 2 hours, followed by (b) 50 rpm in 900 mL of phosphate buffer with 0.3% w/w sodium lauryl sulfate at a pH of 6.8 at 37° C. for another 10 hours.

Para. F. The pharmaceutical composition of any one of Paras. A-E, wherein said tablet or said capsule has a dissolution profile wherein at least about 90% of said ibudilast has been released from said tablet or said capsule at about 24 hours when tested in USP Apparatus Type II at (a) 50 rpm in 900 mL of simulated gastric fluid medium at 37° C. for 2 hours, followed by (b) 50 rpm in 900 mL of phosphate buffer with 0.3% w/w sodium lauryl sulfate at a pH of 6.8 at 37° C. for another 22 hours.

Para. G. The pharmaceutical composition of any one of Paras. A-F, wherein said tablet or said capsule comprises from about 10 mg to about 100 mg of said ibudilast.

Para. H. A pharmaceutical composition comprising ibudilast and at least one pharmaceutically acceptable excipient, wherein said pharmaceutical composition is in the form of a tablet or a capsule, and wherein said tablet or said capsule has a dissolution profile wherein no ibudilast has been released from said tablet or said capsule at about 2 hours when tested in USP Apparatus Type II at 50 rpm in 900 mL of simulated gastric fluid medium at 37° C.

Para. I. The pharmaceutical composition of Para. H, wherein the tablet has a coating comprising methacrylic acid and ethyl acrylate copolymer dispersion; triethyl citrate; and talc.

Para. J. The pharmaceutical composition of Para. H or Para. I, wherein the at least one pharmaceutically acceptable excipient comprises microcrystalline cellulose, lactose, or hypromellose, or any combination of two or more thereof.

Para. K. The pharmaceutical composition of any one of Paras. H-J, wherein said tablet or said capsule has a dissolution profile wherein about 10% to about 20% of said ibudilast has been released from said tablet or said capsule at about 4 hours when tested in USP Apparatus Type II at (a) 50 rpm in 900 mL of simulated gastric fluid medium at 37° C. for 2 hours, followed by (b) 50 rpm in 900 mL of phosphate buffer with 0.3% w/w sodium lauryl sulfate at a pH of 6.8 at 37° C. for another 2 hours.

Para. L. The pharmaceutical composition of any one of Paras. H-K, wherein said tablet or said capsule has a dissolution profile wherein about 55% to about 65% of said ibudilast has been released from said tablet or said capsule at about 12 hours when tested in USP Apparatus Type II at (a) 50 rpm in 900 mL of simulated gastric fluid medium at 37° C. for 2 hours, followed by (b) 50 rpm in 900 mL of phosphate buffer with 0.3% w/w sodium lauryl sulfate at a pH of 6.8 at 37° C. for another 10 hours.

Para. M. The pharmaceutical composition of any one of Paras. H-L, wherein said tablet or said capsule has a dissolution profile wherein about 85% to about 95% of said ibudilast has been released from said tablet or said capsule at about 24 hours when tested in USP Apparatus Type II at (a) 50 rpm in 900 mL of simulated gastric fluid medium at 37° C. for 2 hours, followed by (b) 50 rpm in 900 mL of phosphate buffer with 0.3% w/w sodium lauryl sulfate at a pH of 6.8 at 37° C. for another 22 hours.

Para. N. The pharmaceutical composition of any one of Paras. H-M, wherein said tablet or said capsule comprises from about 10 mg to about 100 mg of said ibudilast.

Para. O. The pharmaceutical composition of any one of Paras. H-N, wherein said tablet or said capsule exhibits an improved $C_{max}$ compared to an intermediate release formulation when administered to a human subject following a dosing protocol consisting of a three-day dose titration phase followed by an eleven-day multiple-dose phase, wherein said tablet or said capsule is administered as a 50-mg dose once daily during the three-day dose titration phase and said tablet or said capsule is administered as a 100-mg dose once daily during the eleven-day multiple-dose phase.

Para. P. A pharmaceutical composition comprising about 3% w/w to about 15% w/w ibudilast, about 30% w/w to about 40% w/w lactose, about 30% w/w to about 40% w/w microcrystalline cellulose, about 15% w/w to about 25% w/w hypromellose, about 0.2% w/w to about 0.8% w/w magnesium stearate, and about 0.5% w/w to about 5% w/w colloidal silicon dioxide.

Para. Q. The pharmaceutical composition of Para. P, wherein the lactose is lactose monohydrate.

Para. R. The pharmaceutical composition of Para. P or Para. Q comprising about 10% w/w ibudilast, about 35% w/w lactose monohydrate, about 33.5% w/w microcrystalline cellulose, about 20% w/w hypromellose, about 0.5% w/w magnesium stearate, and about 1% w/w colloidal silicon dioxide.

Para. S. The pharmaceutical composition of any one of Paras. P-R, wherein the composition is in the form of a tablet.

Para. T. The pharmaceutical composition of Para. S, wherein the tablet has a coating.

Para. U. The pharmaceutical composition of Para. T, wherein the coating comprises polyvinyl alcohol, plasticizer, and pigment.

Para. V. The pharmaceutical composition of Para. T, wherein the coating comprises methacrylic acid and ethyl acrylate copolymer dispersion; triethyl citrate; and talc.

Para. W. The pharmaceutical composition of any one of Paras. P-V, wherein the composition is in the form of a capsule.

Para. X. The pharmaceutical composition of any one of Paras. P-W, wherein the composition is devoid of hydroxypropyl methylcellulose-phthalate.

Para. Y. The pharmaceutical composition of any one of Paras. P-X, wherein the composition is devoid of hydrogenated castor oil.

EQUIVALENTS

It should be understood that although the present disclosure has been specifically disclosed by certain embodiments and optional features, modification, improvement and variation of the disclosures embodied disclosed herein may be resorted to by those skilled in the art, and that such modifications, improvements and variations are considered to be within the scope of this disclosure. The materials, methods, and examples provided here are representative of certain embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

The use of the term "or" in the claims is used to mean "and/or" unless explicitly indicated to refer to alternatives only or the alternatives are mutually exclusive, although the disclosure supports a definition that refers to only alternatives and "and/or."

What is claimed is:

1. A pharmaceutical composition consisting of about 3% w/w to about 15% w/w ibudilast, about 30% w/w to about 40% w/w lactose, about 30% w/w to about 40% w/w microcrystalline cellulose, about 15% w/w to about 25% w/w hypromellose, about 0.2% w/w to about 0.8% w/w magnesium stearate, and about 0.5% w/w to about 5% w/w colloidal silicon dioxide, wherein said pharmaceutical composition is in the form of a tablet or a capsule, and wherein said tablet or said capsule has a dissolution profile wherein at least about 12% of said ibudilast has been released from said tablet or said capsule at about 2 hours when tested in USP Apparatus Type II at 50 rpm in 900 mL of simulated gastric fluid medium at 37° C.

2. The pharmaceutical composition of claim 1, wherein the tablet has a coating comprising polyvinyl alcohol, plasticizer, and pigment.

3. The pharmaceutical composition of claim 1, wherein the at least one pharmaceutically acceptable excipient comprises microcrystalline cellulose, lactose, or hypromellose, or any combination of two or more thereof.

4. The pharmaceutical composition of claim 1, wherein said tablet or said capsule has a dissolution profile wherein at least about 90% of said ibudilast has been released from said tablet or said capsule at about 24 hours when tested in USP Apparatus Type II at (a) 50 rpm in 900 mL of simulated gastric fluid medium at 37° C. for 2 hours, followed by (b) 50 rpm in 900 mL of phosphate buffer with 0.3% w/w sodium lauryl sulfate at a pH of 6.8 at 37° C. for another 22 hours.

5. The pharmaceutical composition of claim 1, wherein said tablet or said capsule comprises from about 10 mg to about 100 mg of said ibudilast.

6. The pharmaceutical composition of claim 1, wherein the lactose is lactose monohydrate.

7. The pharmaceutical composition of claim 1 comprising about 10% w/w ibudilast, about 35% w/w lactose monohydrate, about 33.5% w/w microcrystalline cellulose, about 20% w/w hypromellose, about 0.5% w/w magnesium stearate, and about 1% w/w colloidal silicon dioxide.

8. The pharmaceutical composition of claim 1, wherein the composition is in the form of a tablet.

9. The pharmaceutical composition of claim 8, wherein the tablet has a coating.

10. The pharmaceutical composition of claim 1, wherein the composition is in the form of a capsule.

* * * * *